US006869927B1

(12) United States Patent
Gentz et al.

(10) Patent No.: US 6,869,927 B1
(45) Date of Patent: *Mar. 22, 2005

(54) KERATINOCYTE GROWTH FACTOR-2 FORMULATIONS

(75) Inventors: Reiner L. Gentz, Rockville, MD (US); Arvind Chopra, Gaithersburg, MD (US); Parveen Kaushal, Silver Spring, MD (US); Thomas Spitznagel, Vienna, VA (US); Edward Unsworth, Kensington, MD (US); Fazal Khan, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 375 days.

This patent is subject to a terminal disclaimer.

(21) Appl. No.: 09/585,541

(22) Filed: Jun. 2, 2000

Related U.S. Application Data

(63) Continuation-in-part of application No. 09/218,444, filed on Dec. 22, 1998, now Pat. No. 6,238,888.
(60) Provisional application No. 60/160,913, filed on Oct. 22, 1999, provisional application No. 60/137,448, filed on Jun. 2, 1999, and provisional application No. 60/068,493, filed on Dec. 22, 1997.

(51) Int. Cl.[7] .......................... A01N 37/18; C12P 21/06; A61K 38/00; C12N 15/00; C07H 21/04

(52) U.S. Cl. ................................ 514/2; 514/2; 514/12; 514/925; 435/69.1; 435/69.4; 435/243; 435/320.1; 435/325; 530/300; 530/324; 530/328; 530/399; 530/402; 536/23.51

(58) Field of Search .................. 435/69.4, 69.1, 435/243, 320.1, 325; 514/2, 12, 925; 530/300, 324, 328, 399, 402; 536/23.51

(56) References Cited

U.S. PATENT DOCUMENTS

| 5,194,596 A | 3/1993 | Tischer et al. ............... 530/399 |
| 5,350,836 A | 9/1994 | Kopchick et al. ............ 530/399 |
| 5,580,856 A | 12/1996 | Prestrelski et al. ........... 514/21 |
| 5,677,278 A | 10/1997 | Gospodarowicz et al. .... 514/12 |
| 5,703,047 A | 12/1997 | Wilson ........................ 514/12 |
| 5,731,170 A | 3/1998 | Rubin et al. ............... 435/69.4 |

(List continued on next page.)

FOREIGN PATENT DOCUMENTS

| EP | 0 619 370 A1 | 10/1994 |
| GB | 2 321 852 A | 8/1998 |
| JP | 7-345689 | 12/1995 |

(List continued on next page.)

OTHER PUBLICATIONS

Pending Non–Provisional U.S. patent application Ser. No. 10/194,443, Laird, M.W., filed Jul. 12, 2002 (Not Published).

English language translation of Japanese Patent Application Publication No. 10–330283, Sumitomo Seiyaku Corp., Ltd., filed May 30, 1997 and published Dec. 15, 1998 (Document AP5).

English language translation of Japanese Patent Application Publication No. 10–330284, Sumitomo Seiyaku Corp., Ltd., filed May 30, 1997 and published Dec. 15, 1998 (Document AL6).

(List continued on next page.)

*Primary Examiner*—Bradley L. Sisson
(74) *Attorney, Agent, or Firm*—Human Genome Sciences, Inc.

(57) ABSTRACT

The invention is directed to liquid and lyophilized forms of Keratinocyte Growth Factor-2 (KGF-2) and derivatives thereof. This invention further relates to the formulation of KGF-2 for therapeutic use, for example, to promote or accelerate wound healing.

146 Claims, 8 Drawing Sheets

U.S. PATENT DOCUMENTS

| | | | |
|---|---|---|---|
| 5,773,252 A | 6/1998 | Greene et al. | 435/69.4 |
| 5,773,586 A | 6/1998 | Gospodarowicz et al. | 530/399 |
| 5,814,605 A | 9/1998 | Pierce et al. | 514/12 |
| 5,824,643 A | 10/1998 | Pierce et al. | 514/12 |
| 5,843,883 A | 12/1998 | Gospodarowicz et al. | 514/2 |
| 5,863,767 A | 1/1999 | Gospodarowicz et al. | 435/694 |
| 6,077,692 A | 6/2000 | Ruben et al. | 435/69.4 |
| 6,238,888 B1 * | 5/2001 | Gentz et al. | 435/69.4 |

FOREIGN PATENT DOCUMENTS

| | | |
|---|---|---|
| JP | 8-103240 | 3/1996 |
| JP | 8-214378 | 7/1996 |
| JP | 10-330283 | 12/1998 |
| JP | 10-330284 | 12/1998 |
| JP | 10-330285 | 12/1998 |
| WO | WO 90/08771 | 8/1900 |
| WO | WO 92/14480 | 9/1992 |
| WO | WO 92/22304 | 12/1992 |
| WO | WO 93/21908 | 11/1993 |
| WO | WO 94/22427 | 10/1994 |
| WO | WO 94/23032 | 10/1994 |
| WO | WO 95/01434 | 1/1995 |
| WO | WO 95/03831 | 2/1995 |
| WO | WO 95/24928 A3 | 9/1995 |
| WO | WO 95/24928 | 9/1995 |
| WO | WO 96/11949 | 4/1996 |
| WO | WO 96/11950 | 4/1996 |
| WO | WO 96/11951 | 4/1996 |
| WO | WO 96/11952 | 4/1996 |
| WO | WO 96/22369 | 7/1996 |
| WO | WO 96/25422 | 8/1996 |
| WO | WO 97/20929 | 12/1997 |
| WO | WO 98/06844 | 2/1998 |
| WO | WO 98/16243 | 4/1998 |
| WO | WO 98/16642 | 4/1998 |
| WO | WO 99/32135 | 7/1999 |
| WO | WO 99/41282 | 8/1999 |
| WO | WO 00/72872 | 12/2000 |
| WO | WO 01/02433 | 1/2001 |

OTHER PUBLICATIONS

English language translation of Japanese Patent Application Publication No. 10–330285, Sumitomo Seiyaku Corp., Ltd., filed May 30, 1997 and published Dec. 15, 1998 (Document AM6).

Bowie, J.U., et al., "Deciphering the Message in Protein Sequences: Tolerance to Amino Acid Substitutions," *Science* 247:1306–1310, American Association for the Advancement of Science (1990).

Finch, P.W., et al., "Human KGF Is FGF–Related with Properties of a Paracrine Effector of Epithelial Cell Growth," *Science* 245:752–755, American Association for the Advancement of Science (1989).

Hartung, H., et al., "Murine FGF–12 and FGF–13: expression in embryonic nervous sytem, connective tissue and heart," *Mech. Dev.* 64:31–39, Elsevier Science Ireland Ltd. (Jun. 1997).

Hartung, H., et al., "Assignment of Fgf12 to mouse chromosome bands 16B1→B3 in situ hybridization," *Cytogenet. Cell Genet.* 76:185–186, Karger A.G. (Apr. 1997).

Jimenez, P., et al., "Effect of Topical Keratinocyte Growth Factor–2 on Wound Healing In A Glucocorticoid–Impaired Model," *J. Cutan. Pathol.* 24:105, Munksgaard (Feb. 1997).

Jimenez, P.A., et al., "Effect of Keratinocyte Growth Factor–2 on Cell Proliferation In Vivo," *FASEB J.* 11:A523, Abstract No. 3025, Federation of American Societies for Experimental Biology (Apr. 1997).

Jimenez, P.A. and Rampy, M.A., "Keratinocyte Growth Factor–2 Accelerates Wound Healing in Incisional Wounds," *J. Surg. Res.* 81:238–242, Academic Press, Inc. (Feb. 1999).

Kelley, M.J., et al., "Emergence of the keratinocyte growth factor multigene family during the great ape radiation," *Proc. Natl. Acad. Sci. USA* 89:9287–9291, National Academy of Sciences (1992).

Mason, I.J., et al., "FGF–7 (keratinocyte growth factor) expression during mouse development suggests roles in myogenesis, forebrain regionalisation and epithelial–mesenchymal interactions," *Mech. Dev.* 45:15–30, Elsevier Science Ireland Ltd. (Jan. 1994).

Miyamoto, M., et al., "Molecular Cloning of a Novel Cytokine cDNA Encoding the Ninth Member of the Fibroblast Growth Factor Family, Which Has a Unique Secretion Property," *Mol. Cell. Biol.* 13:4251–4259, American Society for Microbiology (1993).

Ngo, J.T., et al, "Computational Complexity, Protein Structure Prediction, and the Levinthal Paradox," in: *The Protein Folding Problem and Tertiary Structure Prediction*, Merz, Jr., K. and Le Grand, S., eds., Birkhauser, Boston, Massachusetts, pp. 491–495 (1994).

Robson, B. and Garnier, J., "Modern ideas and notations relating to primary structure," in: *Introduction to Proteins and Protein Engineering*, Robson, B. and Garnier, J., eds., Elsevier Science, Amsterdam, The Netherlands, p. 41 (1986).

Ron, D., et al., "Expression of Biologically Active Recombinant Keratinocyte Growth Factor," *J. Biol. Chem.* 268:2984–2988, American Society for Biochemistry and Molecular Biology, Inc. (1993).

Wells, J.A., "Additivity of Mutational Effects in Proteins," *Biochem.* 29:8509–8517, American Chemical Society, (1990).

Yamasaki, M., et al., "Structure and Expression of the Rat mRNA Encoding a Novel Member of the Fibroblast Growth Factor Family," *J. Biol. Chem.* 271:15918–15921, American Society for Biochemistry and Molecular Biology, Inc. (Jul. 1996).

Yan, G., et al., "Sequence of Rat Keratinocyte Growth Factor (Heparin–Binding Growth Factor Type 7)," *In Vitro Cell. Dev. Biol.* 27A:437–438, Tissue Culture Association (1991).

NCBI Entrez, GenBank Report with Revision History, Accession No. M79878, McCombie, W.R. et al., National Center for Biotechnology Information (1992).

NCBI Entrez, GenBank Report with Revision History, Accession No. T52063, Hillier, L. et al., National Center for Biotechnology Information (Feb. 1995).

NCBI Entrez, GenBank Report with Revision History, Accession No. D46201, Sasaki, T. et al., National Center for Biotechnology Information (Aug. 1995).

NCBI Entrez, GenBank Report with Revision History, Accession No. D46420, Sasaki, T. et al., National Center for Biotechnology Information (Aug. 995).

NCBI Entrez, GenBank Report with Revision History, Accession No. D54216, Fujiwara, T. et al., National Center for Biotechnology Information (Sep. 1995).

NCBI Entrez, GenBank Report with Revision History, Accession No. D68729, Kohara, Y. et al., National Center for Biotechnology Information (Dec. 1995).
NCBI Entrez, GenBank Report with Revision History, Accession No. D69248, Kohara, Y. et al., National Center for Biotechnology Information (Dec. 1995).
NCBI Entrez, GenBank Report with Revision History, Accession No. D65627, Kohara, Y. et al., National Center for Biotechnology Information (Dec. 1995).
NCBI Entrez, GenBank Report with Revision History, Accession No. D66221, Kohara, Y. et al., National Center for Biotechnology Information (Dec. 1995).
NCBI Entrez, GenBank Report with Revision History, Accession No. C02000, Okubo, K., National Center for Biotechnology Information (Jul. 1996).
NCBI Entrez, GenBank Report with Revision History, Accession No. W29377, Marra, M. et al., National Center for Biotechnology Information (Sep. 1996).
NCBI Entrez, GenBank Report with Revision History, Accession No. W32720, Hillier, L. et al., National Center for Biotechnology Information (Oct. 1996).
NCBI Entrez, GenBank Report with Revision History, Accession No. W60824, Hillier, L. et al., National Center for Biotechnology Information (Oct. 1996).
NCBI Entrez, GenBank Report with Revision History, Accession No. T70682, Shen, B. et al., National Center for Biotechnology Information (Oct. 1996).
NCBI Entrez, GenBank Report with Revision History, Accession No. AA094753, Liew, C.C., National Center for Biotechnology Information (Oct. 1996).
NCBI Entrez, GenBank Report with Revision History, Accession No. AA133331, Hillier, L. et al., National Center for Biotechnology Information (Nov. 1996).
NCBI Entrez, GenBank Report with Revision History, Accession No. AA190058, Marra, M. et al., National Center for Biotechnology Information (Jan. 1997).
NCBI Entrez, GenBank Report with Revision History, Accession No. AA018953, Hillier, L. et al., National Center for Biotechnology Information (Jan. 1997).
NCBI Entrez, GenBank Report with Revision History, Accession No. AA240978, Marra, M. et al., National Center for Biotechnology Information (Mar. 1997).
NCBI Entrez, GenBank Report with Revision History, Accession No. AA289560, Marra, M. et al., National Center for Biotechnology Information (Apr. 1997).
NCBI Entrez, GenBank Report with Revision History, Accession No. AA296993, Adams, M.D. et al., National Center for Biotechnology Information (Apr. 1997).
NCBI Entrez, GenBank Report with Revision History, Accession No. AA298937, Adams, M.D. et al., National Center for Biotechnology Information (Apr. 1997).
NCBI Entrez, GenBank Report with Revision History, Accession No. AA312184, Adams, M.D. et al., National Center for Biotechnology Information (Apr. 1997).
NCBI Entrez, GenBank Report with Revision History, Accession No. AA312483, Adams, M.D. et al., National Center for Biotechnology Information (Apr. 1997).
NCBI Entrez, GenBank Report with Revision History, Accession No. AA356781, Adams, M.D. et al., National Center for Biotechnology Information (Apr. 1997).
NCBI Entrez, GenBank Report with Revision History, Accession No. AA412789, Marra, M. et al., National Center for Biotechnology Information (May 1997).
NCBI Entrez, GenBank Report with Revision History, Accession No. AA472256, Marra, M. et al., National Center for Biotechnology Information (Jun. 1997).
NCBI Entrez, GenBank Report, Accession No. U67918, Jimenez, P.A. et al., National Center for Biotechnology Information (Jul. 1997).
NCBI Entrez, GenBank Report with Revision History, Accession No. C38464, Kohara, Y. et al., National Center for Biotechnology Information (Sep. 1997).
NCBI Entrez, GenBank Report with Revision History, Accession No. C56505, Kohara, Y. et al., National Center for Biotechnology Information (Sep. 1997).
NCBI Entrez, GenBank Report with Revision History, Accession No. C57074, Kohara, Y. et al., National Center for Biotechnology Information (Sep. 1997).
NCBI Entrez, GenBank Report with Revision History, Accession No. C58558, Kohara, Y. et al., National Center for Biotechnology Information (Sep. 1997).
NCBI Entrez, GenBank Report with Revision History, Accession No. C58846, Kohara, Y. et al., National Center for Biotechnology Information (Sep. 1997).
NCBI Entrez, GenBank Report with Revision History, Accession No. C59317, Kohara, Y. et al., National Center for Biotechnology Information (Sep. 1997).
NCBI Entrez, GenBank Report with Revision History, Accession No. C59311, Kohara, Y. et al., National Center for Biotechnology Information (Sep. 1997).
NCBI Entrez, GenBank Report with Revision History, Accession No. AA605609, Clark, M. et al., National Center for Biotechnology Information (Sep. 1997).
NCBI Entrez, GenBank Report with Revision History, Accession No. AA621871, NCI–CGAP, National Center for Biotechnology Information (Oct. 1997).
NCBI Entrez, GenBank Report with Revision History, Accession No. AA621888, NCI–CGAP, National Center for Biotechnology Information (Oct. 1997).
NCBI Entrez, GenBank Report with Revision History, Accession No. AA675470, Marra, M. et al., National Center for Biotechnology Information (Nov. 1997).
NCBI Entrez, GenBank Report with Revision History, Accession No. AA675519, Marra, M. et al., National Center for Biotechnology Information (Nov. 1997).
NCBI Entrez, GenBank Report with Revision History, Accession No. AA838994, Marra, M. et al., National Center for Biotechnology Information (Feb. 1998).
NCBI Entrez, GenBank Report with Revision History, Accession No. H35048, Lee, N.H. et al., National Center for Biotechnology Information (Apr. 1998).
NCBI Entrez, GenBank Report with Revision History, Accession No. AA906051, NCI–CGAP, National Center for Biotechnology Information (May 1998).
NCBI Entrez, GenBank Report with Revision History, Accession No. C78836, Ko, M.S.H. et al., National Center for Biotechnology Information (Jun. 1998).
English language translation of WO 97/20929 (Document AP4).
English language translation of JP 7–345689 (Document AL3).
English language translation of JP 8–103240 (Document AM3).
English language translation of JP 8–214378 (Document AM4).

Dialog File 351, Accession No. 12329483, Derwent WPI English language abstract for JP 10–330283 (Document AP5).

Dialog File 351, Accession No. 12294894, Derwent WPI English language abstract for JP 10–330284 (Document AL6).

Dialog File 351, Accession No. 12303256, Derwent WPI English language abstract for JP 10–330285 (Document AM6).

International Search Report for International Application No. PCT/US95/01790, mailed Jun. 7, 1995.

Pending Non–Provisional U.S. Appl. No. 09/248,998, Jimenez et al., filed Feb. 12, 1999.

Pending Non–Provisional U.S. Appl. No. 09/345,373, Ruben et al., filed Jul. 1, 1999.

Pending Non-Provisional U.S. Appl. No. 09/853,666, Gentz et al., filed May 14, 2001.

Pending Non–Provisional U.S. Appl. No. 09/610,651, Ruben et al., filed Jun. 30, 2000.

Pending Non–Provisional U.S. Appl. No. 10/035,212, Ruben et al., filed Jan. 4, 2002.

Pending Non–Provisional U.S. Appl. No. 10/075,446, Ruben et al., filed Feb. 15, 2002.

Chen et al. "Stabilization of recombinant human keratinocyte growth factor by osmolytes and salts", J. Pharm. Sciences 85(4):419–422 (1996).

Chen et al. "Aggregation pathway of recombinant human keratinocyte growth factor and its stabilization", Pharmaceutical Research 11(11):1581–1587 (1994).

Scopes, R.K. "Protein Purification: Principles and Practice" ($3^{rd}$. ed.) New York: Springer–Verlag (1994).

Supplementary Partial European Search Report, Application No. EP 98 96 3812, dated Mar. 27, 2003.

Nema et al., "Excipients and their use in injectable products," PDA J. Pharm. Sci. & Tech. 51(4): 166–171 (1997).

* cited by examiner

```
     ATGTGGAAATGGATACTGACACATTGTGCCTCAGCCTTTCCCCACCTGCCCGGCTGCTGC
 1   ---------+---------+---------+---------+---------+---------+   60
     TACACCTTTACCTATGACTGTGTAACACGGAGTGGGAAAGGGGTGGACGGGCCGACGACG

M  W  K  W  I  L  T  H  C  A  S  A  F  P  H  L  P  G  C  C

TGCTGCTGCTTTTTGTTGCTGTCTTGGTGTCTTCCGTCCCTGTCACCTGCCAAGCCCTT
 61  ---------+---------+---------+---------+---------+---------+   120
     ACGACGACGAAAAACAACGACAGAACCACAGAAGGCAGGGACAGTGGACGGTTCGGGAA

C  C  C  F  L  L  F  L  V  S  S  V  P  V  T  C  Q  A  L

GGTCAGGACATGGTGTCACCAGAGGCCACCAACTCTTCTTCCTCCTCCTCTCCT
 121 ---------+---------+---------+---------+---------+---------+   180
     CCAGTCCTGTACCACAGTGGTCTCCGGTGGTTGAGAAGAAGGAGGAAGAGGAGGA

G  Q  D  M  V  S  P  E  A  T  N  S  S  S  S  F  S  S  P

TCCAGGCGCGGGAAGGCATGtGCGGAGCTACAATCACCTTCAAGGAGATGTCCGCTGGAGA
 181 ---------+---------+---------+---------+---------+---------+   240
     AGGTCGCGCCCCTTCCGTACACGCCTCGATGTTAGTGGAAGTTCCTCTACAGGCGACCTCT

S  S  A  G  R  H  V  R  S  Y  N  H  L  Q  G  D  V  R  W  R

MATCH WITH FIG.1B
```

FIG.1A

MATCH WITH FIG.1A

```
     AAGCTATTCTCTTTCACCAAGTACTTTCTCAAGATTGAGAAGAACGGGAAGGTCAGCGGG
241  ------+---------+---------+---------+---------+---------+  300
     TTCGATAAGAGAAAGTGGTTCATGAAAGAGTTCTAACTCTTCTTGCCCTTCCAGTCGCCC

K   L   F   S   F   T   K   Y   F   L   K   I   E   K   N   G   K   V   S   G

ACCAAGAAGGAGAACTGCCCGTACAGCATCCTGGAGATAACATCAGTAGAAATCGGAGTT
301  ------+---------+---------+---------+---------+---------+  360
     TGGTTCTTCCTCTTGACGGGCATGTCGTAGGACCTCTATTGTAGTCATCTTTAGCCTCAA

T   K   K   E   N   C   P   Y   S   I   L   E   I   T   S   V   E   I   G   V

GTTGCGGTCAAAGCCATTAACAGCAACTATTACTTAGCCATGAACAAGAAGGGGAAACTC
361  ------+---------+---------+---------+---------+---------+  420
     CAACGGCAGTTTCGGTAATTGTCGTTGATAATGAATCGGTACTTGTTCTTCCCCTTTGAG

V   A   V   K   A   I   N   S   N   Y   Y   L   A   M   N   K   K   G   K   L

TATGGCTCAAAAGAATTTAACAATGACTGTAAGCTGAAGGAGAGGATAGAGGAAAATGGA
421  ------+---------+---------+---------+---------+---------+  480
     ATACCGAGTTTTCTTAAATTGTTACTGACATTCGACTTCCTCTCCTATCTCCTTTTACCT

Y   G   S   K   E   F   N   N   D   C   K   L   K   E   R   I   E   E   N   G
```

MATCH WITH FIG.1C

FIG.1B

MATCH WITH FIG. 1B

```
481 TACAATACCTATGCATCATTTAACTGGCAGCATAATGGGAGGCAAATGTATGTGGCATTG 540
    ----+----+----+----+----+----+----+----+----+----+----+----+
    ATGTTATGGATACGTAGTAAATTGACCGTCGTATTACCCTCCGTTTACATACACCGTAAC
     Y  N  T  Y  A  S  F  N  W  Q  H  N  G  R  Q  M  Y  V  A  L

541 AATGGAAAAGGAGCTCCAAGGAGAGAGGACAGAAAAACGAAGGAAAAACACCTCTGCTCAC 600
    ----+----+----+----+----+----+----+----+----+----+----+----+
    TTACCTTTTCCTCGAGGTTCCTCTCCTGTCTTTTTGCTTCCTTTTTGTGGAGACGAGTG
     N  G  K  G  A  P  R  R  G  Q  K  T  R  R  K  N  T  S  A  H

601 TTTCTTCCAATGGTGGTACACTCATAG 627
    ----+----+----+----+----+--
    AAAGAAGGTTACCACCATGTGAGTATC
     F  L  P  M  V  V  H  S  *
```

FIG.1C

KERATINOCYTE GROWTH FACTOR-2 FORMULATIONS

CROSS-REFERENCE TO RELATED APPLICATIONS

This application is a continuation-in-part of U.S. application Ser. No. 09/218,444, filed Dec. 22, 1998, now U.S. Pat. No. 6,238,888, issued May 29, 2001, and claims the benefit of priority of the filing date of U.S. application Ser. No. 60/068,493 filed on Dec. 22, 1997, abandoned, U.S. application Ser. No. 60/137,448, filed Jun. 2, 1999, abandoned and U.S. application Ser. No. 60/160,913, filed Oct. 22, 1999, abandoned; the disclosures of all of which are incorporated by reference herein.

BACKGROUND OF THE INVENTION

1. Field of the Invention

The present invention is directed to liquid and lyophilized formulations of Keratinocyte Growth Factor-2 (KGF-2) and derivatives thereof. This invention further relates to formulations of KGF-2, especially topical and injectable formulations, that can be employed for therapeutic use in indications requiring soft-tissue growth and regeneration.

2. Related Art

The fibroblast growth factor family has emerged as a large family of growth factors involved in soft-tissue growth and regeneration. It presently includes several members that share a varying degree of homology at the protein level, and that, with one exception, appear to have a similar broad mitogenic spectrum, i.e., they promote the proliferation of a variety of cells of mesodermal and neuroectodermal origin and/or promote angiogenesis.

KGF was originally identified as a member of the FGF family by sequence homology or factor purification and cloning. Keratinocyte growth factor (KGF) was isolated as a mitogen from a cultured murine keratinocyte line (Rubin, J. S. et al., *Proc. Natl. Acad. Sci. USA* 86:802–806 (1989)). Unlike the other members of the FGF family, it has little activity on mesenchyme-derived cells but stimulates the growth of epithelial cells. Keratinocyte growth factor is produced by fibroblasts derived from skin and fetal lung (Rubin et al. (1989)). The Keratinocyte growth factor mRNA was found to be expressed in adult kidney, colon and ilium, but not in brain or lung (Finch, P. W. et al. *Science* 245:752–755 (1989)). KGF displays the conserved regions within the FGF protein family. KGF binds to the FGF-2 receptor with high affinity.

Impaired wound healing is a significant source of morbidity and may result in such complications as dehiscence, anastomotic breakdown and, non-healing wounds. In the normal individual, wound healing is achieved uncomplicated. In contrast, impaired healing is associated with several conditions such as diabetes, infection, immunosuppression, obesity and malnutrition (Cruse, P. J. and Foord, R., *Arch. Surg.* 107:206 (1973); Schrock, T. R. et al., *Ann. Surg.* 177:513 (1973); Poole, G. U., Jr., *Surgery* 97:631 (1985); Irvin, G. L. et al., *Am. Surg.* 51:418 (1985)).

Wound repair is the result of complex interactions and biologic processes. Three phases have been described in normal wound healing: acute inflammatory phase, extracellular matrix and collagen synthesis, and remodeling (Peacock, E. E., Jr., *Wound Repair*, 2nd edition, W B Saunders, Philadelphia (1984)). The process involves the interaction of keratinocytes, fibroblasts and inflammatory cells at the wound site.

It is desirable to formulate polypeptides that are capable of promoting and enhancing soft-tissue growth and regeneration in pharmaceutical compositions that (1) are stable over prolonged periods of storage, (2) increase the pharmacological activity or effectiveness of the polypeptide and/or (3) allow facile application or administration of the polypeptide in therapeutic regimens.

SUMMARY OF THE INVENTION

The present invention is directed to liquid and lyophilized formulations of KGF-2 and deletion or point or substitution mutants thereof (referred to herein as KGF-2 polypeptides). This invention further relates to the use of such formulations of KGF-2 polypeptides to promote or accelerate soft tissue growth or regeneration, for example in wound healing, or in treating mucocytis or inflammatory bowel disease. Preferred formulations of the present invention employ novel mutant forms of KGF-2, and in one embodiment employ a deletion mutant referred to herein as KGF2-Δ33. The co-ingredients employed in the formulations (1) provide storage stability to the KGF-2 polypeptide, (2) further enhance soft-tissue healing activity of the therapeutic composition, and/or (3) provide the KGF-2 polypeptide in an active form while allowing facile application and administration for particular therapeutic purposes.

A first aspect of the present invention relates to a formulation comprising a KGF-2 polypeptide and a buffering agent having a buffering capacity of between about pH 5.0 and about pH 8.0. Useful buffers include phosphate, acetate, aconitate, succinate, malate, carbonate and citrate buffers, citrate being preferred.

A second aspect of the invention relates to a formulation comprising a KGF-2 polypeptide, a lyophilization bulking agent and a buffering agent having a buffering capacity of between about pH 5.0 and about pH 8.0. Useful buffers include phosphate, aconitate, succinate, malate, carbonate and citrate buffers, citrate being preferred.

A third aspect of the invention relates to a formulation comprising a KGF-2 polypeptide and a thiol-containing compound, preferably monothioglycerol, capable of stabilizing the KGF-2 polypeptide. This formulation preferably includes a buffering agent having a buffering capacity of between about pH 5.0 and about pH 8.0. This formulation may also include one or more antioxidants and or one or more metal chelating agents.

A fourth aspect of the present invention relates to a formulation comprising a KGF-2 polypeptide, a buffer, and a high molecular weight compound that causes the formulation to gel at a certain predefined temperature. A preferred high molecular weight compound is a Pluronic or Poloxamer polyoxyethylene-polyoxypropylene block copolymer. A thiol-containing compound, such as monothioglycerol, can be included in the formulation to provide added stability to the polypeptide.

A fifth aspect of the present invention relates to a formulation comprising a KGF-2 polypeptide, a buffering agent and a thickening agent. Thickening agents are used to increase the viscosity of the formulation. Preferred thickening agents are carboxymethyl cellulose (CMC), hydroxyethyl cellulose (HEC), hydroxypropylmethyl cellulose (HPMC), Natrosol, and Carbomers.

In addition, the formulations of the present invention may also include metal chelating agents, antioxidants or thiol-containing compounds, such as ascorbic acid ester, monothioglycerol, cysteine, tocopherols, butylated hydroxyanisole, sodium sulphate, sodium bisulfite, and sodium metasulfite and preservatives such as m-cresol, phenol, chlorobutane, chlorobutanol, benzylalcohol, methyl parabens and propyl parabens. Anti-microbial preservatives may decrease the stability of KGF-2 formulations. Surprisingly, a combination of methyl paraben and propyl paraben was found to be suitable for use in KGF-2 formulations. The formulations of the present invention may also have an nitrogen blanket overlay on the head space of the vial. Additionally, the formulations of the present invention may be include purging the formulation buffer with helium, argon, or nitrogen.

BRIEF DESCRIPTION OF THE FIGURES

FIGS. 1A–1C illustrate the cDNA and corresponding deduced amino acid sequence of KGF-2. The initial 35 or 36 amino acid residues represent the putative leader sequence (underlined). The standard one letter abbreviations for amino acids are used. Sequencing inaccuracies are a common problem when attempting to determine polynucleotide sequences. Sequencing was performed using a 373 Automated DNA sequencer (Applied Biosystems, Inc.). Sequencing accuracy is predicted to be greater than 97% accurate. (SEQ ID NOs:1 and 2).

FIG. 2(A) shows stimulation of normal primary epidermal keratinocyte proliferation by KGF-2. FIG. 2(B) shows the stimulation of normal primary epidermal keratinocyte proliferation by KGF-2 Δ33. FIG. 2(C) shows the stimulation of normal primary epidermal keratinocyte proliferation by KGF-2 Δ28.

DETAILED DESCRIPTION OF THE PREFERRED EMBODIMENTS

Figure 2A:
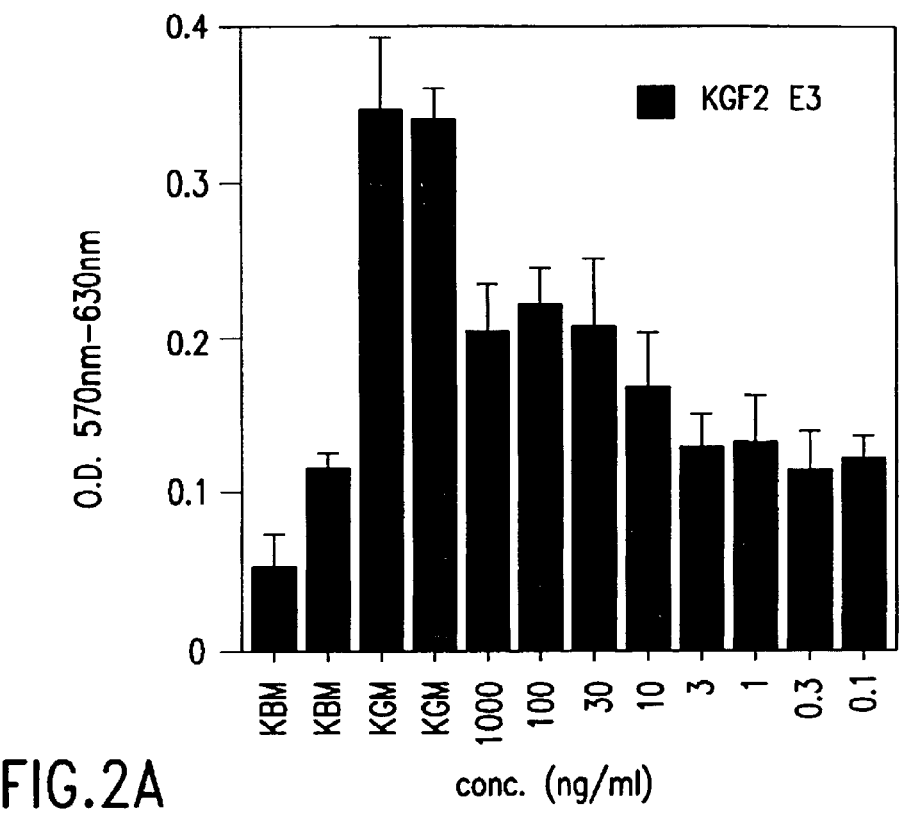
FIGS. 2(A)–2(C) depict stimulation of normal primary epidermal keratinocyte proliferation by KGF-2 polypeptides of the invention.
Figure 2B:
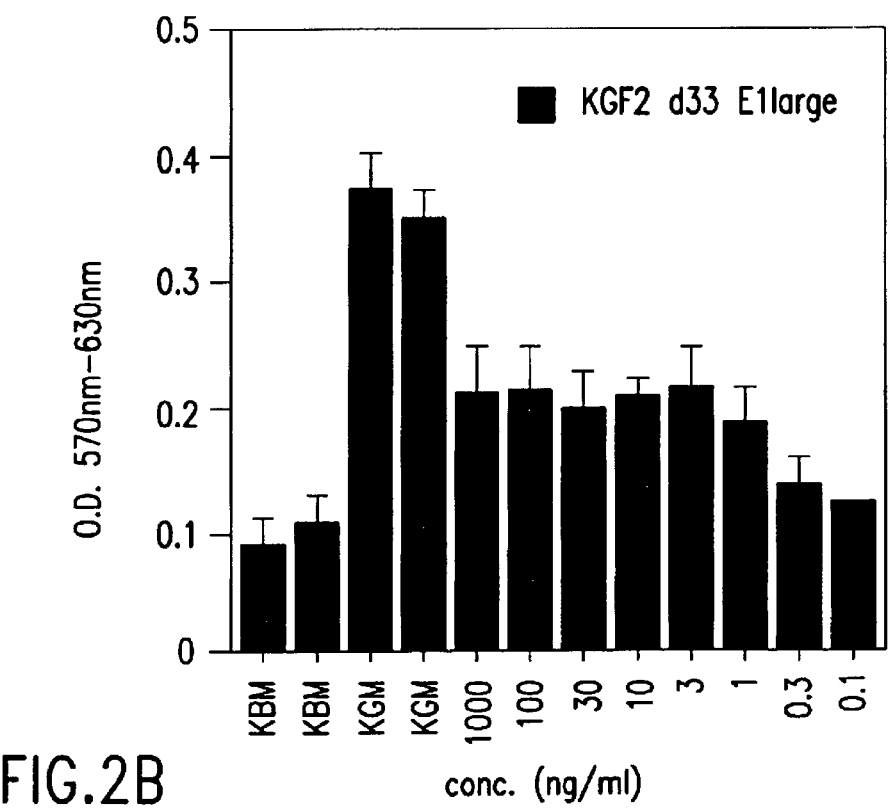
Figure 2C:
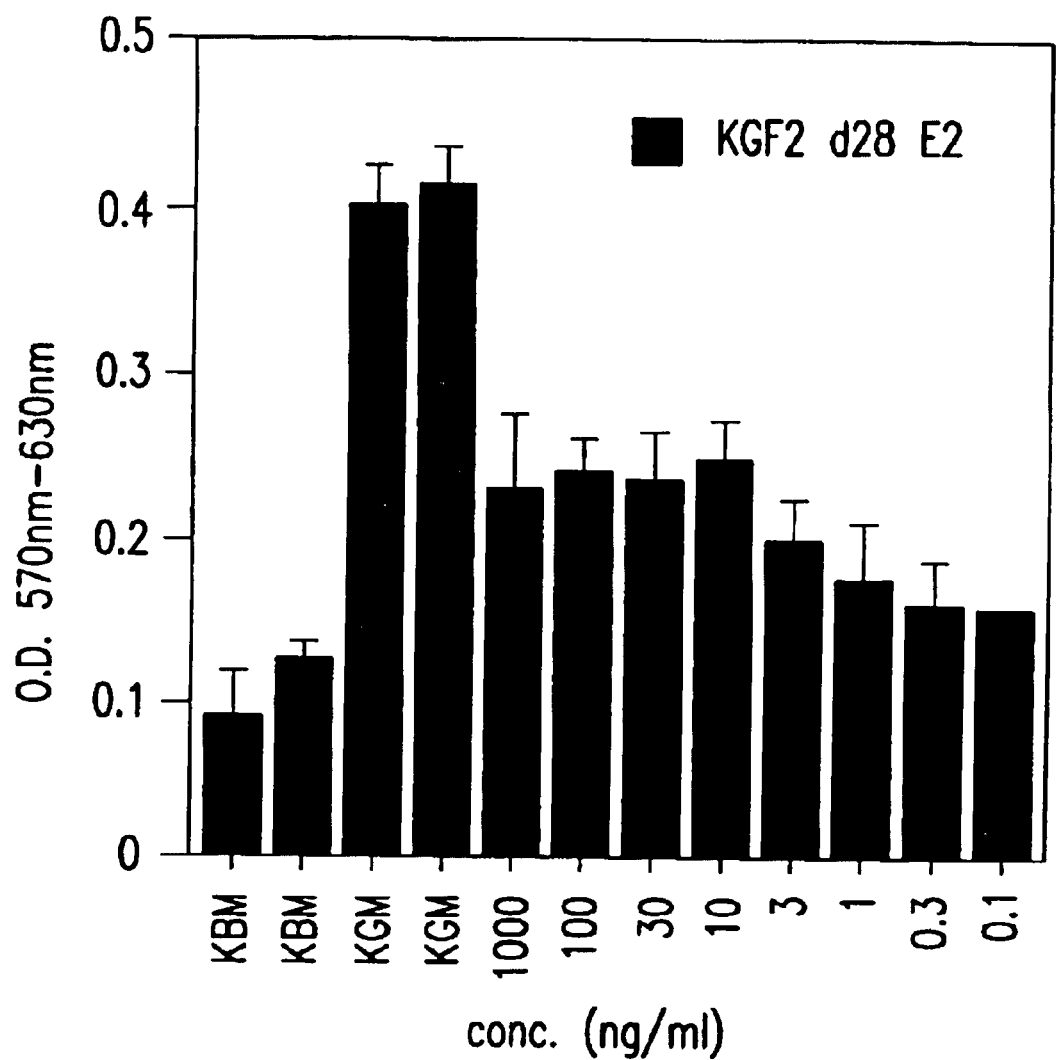

KGF-2 stimulates the proliferation of epidermal keratinocytes but not mesenchymal cells such as fibroblasts. Thus, "a polypeptide having KGF-2 protein-like activity" includes polypeptides that exhibit the KGF-2 activity, in the keratinocyte proliferation assay set forth below and bind to FGF receptor isoforms 1-iiib and 2-iiib.

The present invention is directed to pharmaceutical and veterinary formulations of KGF-2 polypeptides. The KGF-2 polypeptides are defined herein by reference to the polypeptide of FIG. 1 (SEQ ID NO:2) or that encoded by the deposited cDNA, and include fragments, derivatives and analogs of the polypeptide of FIG. 1 (SEQ ID NO:2) or that encoded by the deposited cDNA which retain essentially the same biological function as the parent polypeptide. The polypeptides employed in the present invention may be recombinant polypeptides, natural polypeptides or synthetic polypeptides, preferably recombinant polypeptides.

It has been discovered that KGF-2 polypeptides exhibit poor activity and stability at a pH of 4.5 or less, or at a pH above about 8.0. The present inventors have discovered that KGF-2 polypeptides oxidize and precipitate. These polypeptides present a difficult challenge when attempting to formulate them for therapeutic purposes. In order to maintain physico-chemical properties and biological activity, KGF-2 polypeptides can be formulated with antioxidants, such as oxygen scavenging compounds, and/or a protein stabilizer, such as a thiol-containing compound, and/or a metal-chelating agent, such as EDTA. Stabilization, as used herein, refers to the maintenance of both physico-chemical properties and substantial biological activity of the KGF-2 polypeptides over a given time period.

The formulations according to the present invention include gel, thickened solution, solution and lyophilized forms. Formulations are also referred to herein as "pharmaceutical compositions" or "compositions."

Injectable Formulations

Liquid Formulations

A first aspect of the present invention is directed to liquid formulations of KGF-2 polypeptides that comprise: a KGF-2 polypeptide and a buffer having a buffering capacity of between about pH 5.0 and about pH 8.0, more preferably pH 5.5 to pH 6.5, most preferably pH 6.2. Useful buffers include buffers derived from phosphate, acetic, aconitic, citric, glutaric, malic, succinic and carbonic acids. Typically employed is an alkali or alkaline earth salt of one of the aformentioned acids. More preferably the buffer will be acetate or citrate, most preferably citrate. For example, the formulation may comprise a composition formed by mixing a buffering amount of citric acid or a pharmaceutically acceptable salt thereof with KGF-2 Δ33 in water. The formulation alternatively may comprise a composition formed by mixing a buffering amount of acetic acid or a pharmaceutically acceptable salt thereof with KGF-2 Δ33 in water. Preferable buffer concentrations are from about 5 mM to about 50 mM. Most preferably the acetate buffer will have a concentration of about 20 mM and the citrate buffer will be about 10 mM to about 20 mM. The formulation may also include NaCl, glycine, sucrose or mannitol, or combinations thereof, as a tonicifier at a concentration of from about 0 mM to about 150 mM, preferably 10 to about 150 mM, most preferably at about 125 mM, and a metal chelating agent, such as EDTA, at a concentration of from about 0 mM to about 10 mM, most preferably at about 1 mM. Additionally, a liquid formulation of the present invention may also include one or more of (a) a stabilizing amount of an antioxidant, such as ascorbate and/or (b) a protein stabilizing amount a thiol-compound, for example monothioglycerol (MTG). Without wishing to be bound by theory, it is believed that thiol compounds such as MTG serve to protect free sulfhydryl groups present in the KGF-polypeptides. The storage conditions for the liquid formulation are typically at about 2° C. to about 8° C. Alternatively, storage conditions are at or below −20° C. Most preferably, storage conditions are at about −20° C. Maintaining a KGF-2 liquid formulation in a frozen state limits the amount of oxidation to the polypeptide which in turn results in a stable polypeptide formulation.

Preferably, a liquid formulation comprises:

(1) a therapeutically-effective amount of a KGF-2 polypeptide;

(2) an effective amount of a buffer having a buffering capacity of between about pH 5.0 and about pH 8.0; and (3) a pharmaceutically acceptable diluent; and (4) optionally one or more of the following:
 (a) NaCl, glycine, sucrose or mannitol or combinations thereof as a tonicifier,
 (b) a chelating agent,
 (c) a stabilizing amount of an antioxidant, and
 (d) a stabilizing amount of a protein stabilizer.

The KGF-2 polypeptide preferably is maintained in solution.

Compositions of the present invention are manufactured by admixing the above listed ingredients together, preferably in concentrations and ratios as expressed herein.

Antioxidants that can be used in the liquid formulation include sodium bisulfate, cysteine, sodium sulfite, ascorbic acid, tocopherols, and butylated hydroxyanisole. In addition, stabilizers that can be used in the liquid formulation also include thiols such as cysteine, methionine and thioglycerols. Chelating agents that can be employed include ethylenediamine tetraacetic acid (EDTA), or diethylenetriamine pentaacetic acid (DPTA), with EDTA being preferred.

Formulations of the present invention which include antioxidants or thiols can increase the stability of the KGF-2 polypeptides. This makes it possible to have a pharmaceutical product with a longer shelf life.

Additionally, the formulations of the present invention may further include one or more preservatives, such as benzyl alcohol, preferably at a concentration of about 0.5% to about 1.5%, most preferably at a concentration of about 0.9%; chlorobutanol, preferably at a concentration of about 0.01% to about 1%, most preferably about 0.5%; methyl paraben, preferably at a concentration of about 0.1% to about 0.2%, most preferably at about 0.18%; propyl paraben, preferably at a concentration of about 0.01% to about 0.05%, most preferably about 0.02%, m-cresol, preferably at a concentration of about 0.1% to about 1%, most preferably about 0.3%; and/orphenol, preferably at aconcentration of about 0.1% to about 1%, most preferably at about 0.5%. Particularly preferred is methyl paraben and propyl paraben used together; with methyl paraben at a concentration of about 0.1% to about 0.2% and propyl paraben at a concentration of about 0.10% to about 0.05%. Most preferred is a combination of methyl paraben and propyl paraben, with methyl paraben at a concentration of 0.18% and propyl paraben at a concentration of 0.02%.

More preferred liquid formulations comprise:
  (1) a KGF-2 polypeptide in a concentration range of about 0.02 to about 40 mg/ml (w/v), more preferably about 0.05 to about 30 mg/ml (w/v), even more preferably about 0.1 to about 20 mg/ml (w/v), still more preferably about 10 mg/ml (w/v), and most preferably about 0.2 to 4 mg/ml;
  (2) a buffer having a buffering capacity of between about pH 5.0 and about pH 8.0 at a concentration range of about 5 mM to about 50 mM, preferably about 5 mM to about 30 mM; and
  (3) a pharmaceutically acceptable diluent, preferably water, to bring the composition to a designated volume.

Useful buffers for the formulations of the present invention include buffers derived from acetic, aconitic, citric, glutaric, malic, succinic, phosphate and carbonic acids. Typically employed is an alkali or alkaline earth salt of one of the aforementioned acids. Acetate and citrate buffers, such as acetic acid or a pharmaceutically acceptable salt thereof, or citric acid or a pharmaceutically acceptable salt thereof, are preferred. The preferable pH ranges for the solution formulation is from about pH 5.0 to about pH 8.0, preferably pH 5.5 to pH 6.5, and most preferably about pH 6.2. Sodium acetate or sodium citrate are the preferred buffering agents, with sodium citrate being most preferred.

To the above solution also preferably added are:
  (4) a chelating agent, such as EDTA at a concentration range of about 0.1 mM to about 10 mM, more preferably at about 1 mM;
  (5) a tonicifier, such as NaCl, glycine, sucrose or mannitol, or combinations thereof at a concentration range of about 0.01 mM to about 150 mM and more preferably at about 125 mM.

Optionally, a liquid formulation may also include a protein stabilizing amount of a compound selected from the group consisting of:
  (a) about 0.5% to about 2% w/v glycerol,
  (b) about 0.1% to about 1% w/v methionine, or
  (c) about 0.1% to about 2% w/v monothioglycerol.

Preferred embodiments of this aspect of the present invention include a composition formed by mixing:
  (1) a KGF-2 polypeptide in a concentration of about 0.02 to about 40 mg/ml (w/v), more preferably about 0.1 to about 20 mg/ml, and most preferably about 0.2 to 4 mg/ml.
  (2) 10 mM sodium citrate or 20 mM sodium acetate;
  (3) 125 mM NaCl;
  (4) 1 mM EDTA; and
  (5) water as diluent.

More preferably, the solution formulation comprises a composition formed by mixing:
  (1) about 0.2 to about 4 mg/ml of a KGF-2 polypeptide;
  (2) 20 mM sodium acetate;
  (3) 125 mM NaCl;
  (4) 1 mM EDTA; and
  (5) water as a diluent,
wherein the solution is at about pH 6.2 and is stored at about −20° C.

Most preferably, the solution formulation comprises a composition formed by mixing:
  (1) about 1.0 mg/ml of a KGF-2 polypeptide;
  (2) 20 mM citrate, pH 5–5.5; and
  (3) 0.01% polysorbate 80.

The solution preferably also includes either about 7% sucrose or a combination of 2% glycine and 0.5% sucrose.

Alternatively, the solution formulation comprises a composition formed by mixing:
  (1) about 1.0 mg/ml of a KGF-2 polypeptide;
  (2) 20 mM citrate, pH 5–5.5;
  (3) 1 mM EDTA; and
  (4) 0.01% polysorbate 80.

The solution preferably also includes either about 7% sucrose or a combination of 2% glycine and 0.5% sucrose.

The present inventors have discovered that KGF-2 polypeptides readily oxidize, aggregate and precipitate out of solution. Although oxidation of KGF-2 does not destroy biological activity, limiting the extent of oxidation of the product leads to a more stable product. The inventors observed that if the liquid formulation is at a pH too low the KGF-2 polypeptide will lose biological activity. Additionally, as the pH of the solution approaches the pI for KGF-2, the protein will precipitate out of solution. Thus, the inventors have determined that liquid formulations should be maintained in the range of about pH 6.0 to about pH 7.0, and that a pH of about 6.2 is most optimal for stabilizing the KGF-2 polypeptide. Moreover, the inventors surprisingly determined that a citrate buffer specifically stabilizes the KGF-2 polypeptides.

Although, the use of a citrate buffer having at about pH 6.0–6.2 provides a liquid formulation that reduces aggregation of the KGF-2 polypeptide and increases stability, the liquid polypeptide formulation may still be subject to oxidation and precipitation of KGF-2 polypeptides. Thus, the inventors developed a lyophilized formulation as set forth below.

Lyophilized Formulations

A second aspect of the present invention is directed to lyophilizated formulations of KGF-2 polypeptides that comprise: a KGF-2 polypeptide and a buffer having a buffering capacity of between about pH 5.0 and about pH 8.0, more preferably pH 5.5 to pH 6.5, most preferably pH 6.2. Useful buffers include buffers derived from phosphate, aconitic, citric, glutaric, malic, succinic and carbonic acids. Typically employed is an alkali or alkaline earth salt of one of the aforementioned acids. More preferably the buffer will be phosphate or citrate, most preferably citrate. For example, the formulation may comprise a composition formed by mixing a buffering amount of citric acid or a pharmaceutically acceptable salt thereof with KGF-2 Δ33 in water. The preferable buffer concentration is from about 5 mM to about 50 mM and more preferably at about 10 mM. Most preferably, the citrate buffer will be added in a concentration of about 10 mM. Also preferably included in the formulation is NaCl as a tonicifier at a concentration of from about 0 mM to about 150 mM, most preferably at about 20 mM and a metal chelating agent, such as EDTA, at a concentration of from about 0 mM to about 10 mM, most preferably at about 1 mM. In addition, bulking agents/cryoprotectants such as sucrose, glycine, mannitol, trehalose or other pharmaceutically acceptable bulking agents are included in the formulation. The amount of bulking agent used will be such that the solution is isotonic and is in a range of about 2% to about 10% w/v. Preferred concentrations are as follows: 5% mannitol, 7% sucrose, 8% trehalose, or 2% glycine+0.5% sucrose. More preferably, sucrose or sucrose/glycine mixture is used. Additionally, a lyophilized formulation of the present invention may also include one or more of (a) a stabilizing amount of an antioxidant, such as ascorbate or (b) a stabilizing amount of thiol-compound, for example monothioglycerol. Storage conditions for the lyophilized formulation are typically at about 2° C. to about 25° C. More preferably storage conditions are at or below about 2° C. to about 8° C.

KGF-2 polypeptides are lyophilized at a concentration of about 0.02 mg/ml to about 10 mg/ml of protein in the initial solution The initial lyophilization solution preferably comprises (in addition to the KGF-2 polypeptides):

(1) an effective amount of citric acid or a pharmaceutically acceptable salt thereof, preferably sodium citrate, at a concentration range of about 5 mM to about 20 mM;

(2) NaCl at a concentration range of about 0 mM to about 125 mM, (3) EDTA at a concentration range of about 0 mM to about 10 mM, (4) one or more of sucrose, mannitol, glycine or trehalose or mixtures thereof at a concentration range of about 2% w/v to about 15% w/v; and (5) water.

The preferred pH range for the lyophilization buffer is from about 5.5 to about 8.0, preferably about pH 6.2.

More preferably, the lyophilization buffer comprises 10 mM sodium citrate, 20 mM sodium chloride, 1 mM disodium EDTA at pH 6.2 and 7% sucrose.

The lyophilized KGF-2 polypeptide formulations are reconstituted in sterile water so as to maintain isotonic conditions of about 290 mOsm. The KGF-2 polypeptides can be reconstituted in sterile water, optionally containing a stabilizing amount of antioxidants comprising: a) about 0.01% to about 2% w/v monothioglycerol, b) about 0.01% to about 2% w/v ascorbic acid, c) about 0.01% to about 2% w/v methionine or d) combinations thereof.

The present invention includes lyophilization cycles that yield a stable KGF-2 polypeptide formulation. The lyophilization cycle is designed to keep the KGF-2 polypeptide product below its collapse temperature during the primary drying phase. Additionally, the moisture content is targeted to be preferably less than 5%, and more preferably less than 2%. Such a protocol must be determined for any particular protein on an individual basis. An example lyophilization cycle for the KGF-2 sucrose containing lyophilization formulation according to the present invention was determined to be as follows:

| Temperature (° C.) | Pressure (mTorr) | Time (min.) |
|---|---|---|
| 5 (hold) | atmospheric | 60 |
| 5 to −45 (ramp) | atmospheric | 120 |
| −45 (hold) | atmospheric | 120 |
| −45 (hold) | 75 to 100 | 60 |
| −45 to −20 (ramp) | 75 to 100 | 125 |
| −20 (hold) | 75 to 100 | 2100 |
| −20 to +25 (ramp) | 75 to 100 | 225 |
| +25 (hold) | 75 to 100 | 1020 |

Another example lyophilization cycle for the KGF-2 lyophilization formulation according to the present invention was determined to be as follows:

| Temperature (° C.) | Pressure (mTorr) | Time (min.) |
|---|---|---|
| 5 (hold) | atmospheric | 60 |
| 5 to −45 (ramp) | atmospheric | 120 |
| −45 (hold) | atmospheric | 120 |
| −45 (hold) | 75 to 100 | 180 |
| −45 to −30 (ramp) | 30 | 120 |
| −30 (hold) | 30 | 4200 |
| −20 to +25 (ramp) | 100 | 60 |
| +25 (hold) | 100 | 960 |

Figure 4:
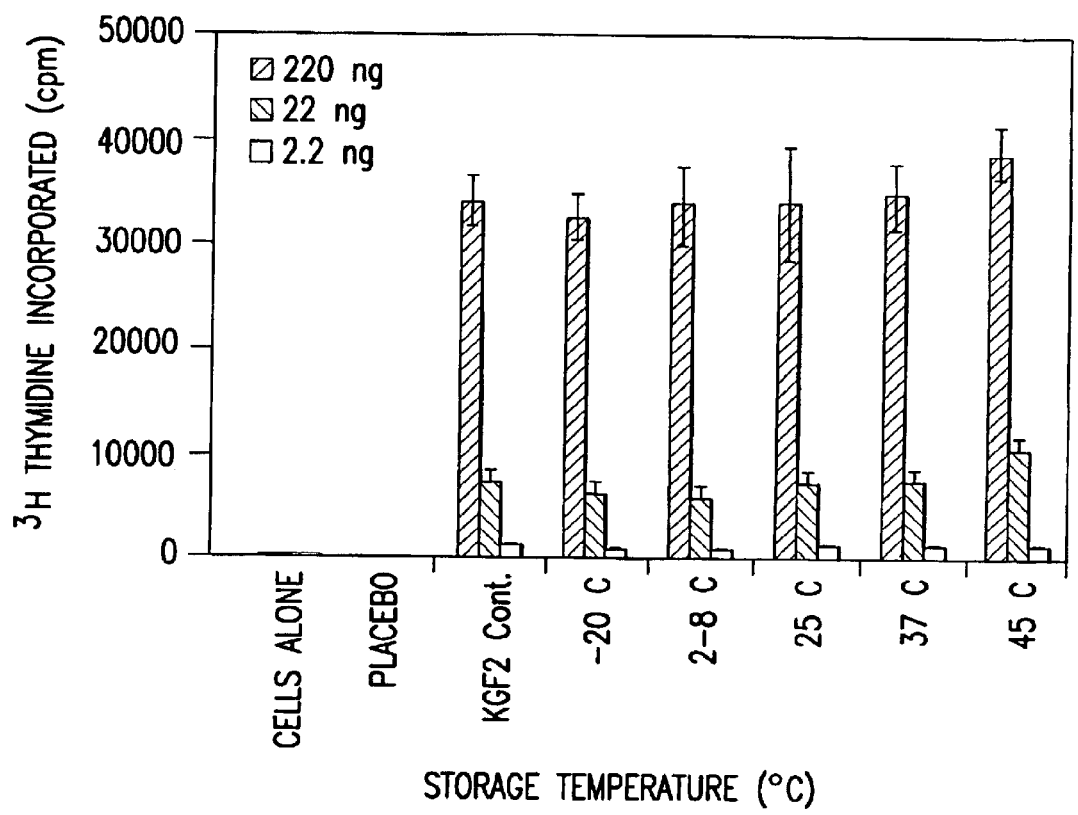
FIG. 4 shows bioactivity results for KGF-2 Δ33 lyophilized preparation, 9 month stability.

The lyophilization formulation of the present invention provides a product with unexpectedly increased stability. Indeed, lyophilized KGF-2 formulations of the present invention are biologically stable for at least 9 months at temperatures of up to 45° C. (FIG. 4). Reverse-phase HPLC demonstrated that the lyophilized KGF-2 formulations of the present invention retained its physio-chemical properties for up to 8 months at temperatures of at or below 45° C. and 75% relative humidity. Stability for this length of time at such high temperatures is very unusual for proteins.

Thickened and Gel Formulations

A third aspect of the invention is directed to thickened or gel formulations for KGF-2 polypeptides.

1) Thickening Agents:

Thickening agents may be added to the above described liquid formulations to increase the viscosity of the resulting formulation. A formulation having an increased viscosity may be beneficial for topical applications where controlled release, adhering to the shape of a wound or avoiding run-off may be important. Such thickened formulations are employed for topical uses such as wound healing, to treat skin disorders or any other use which could be treated via topical application of a KGF-2 pharmaceutical composition.

The thickening agent should raise the viscosity to about 50 to about 10,000 centipoise (cps), more preferably about 50 to about 1,000 cps and most preferably about 200 to about 300 cps. Viscosity is measured using a rotating spindle viscometer. The most preferred concentration of thickening agent is 0 to 5% (w/w). The thickened solution will stay liquid at all times.

Examples of appropriate thickening agents include, but are not limited to water soluble etherified celluloses and carbomer (high molecular weight polymers of acrylic acid cross-linked with either allylsucrose or allyl ethers of pentaerythritol). Examples of etherified cellulose are well known in the art (listed in USP) and include alkyl celluloses, hydroxyalkyl celluloses and alkylhydroxyalkyl celluloses e.g., methylcellulose, hydroxyethyl cellulose, hydroxy propyl cellulose, hydroxy propyl methylcellulose, and the like. In a further embodiment, the topical or incisional gel may comprise about 0 to about 20% by weight of a cellulose derivative having a molecular weight of about 50,000 to about 700,000. In a preferred embodiment the cellulose derivative is present at about 2% to about 8% by weight and has a molecular weight in the range of about 80,000 to about 240,000. Preferred cellulose derivatives are hydroxypropylmethyl cellulose, methyl cellulose, carboxymethyl cellulose, and hydroxyethyl cellulose.

When thickening agents are added to the injectable formulations, detailed above, salts and buffering agents may be added or removed from the formulation for optimal stability. For example, the citrate concentration may be increased. Preferred concentrations for citrate are for example, about 10 mM to about 500 mM citrate, more preferably about 10 mM to about 50 mM citrate and most preferably about 10 mM to about 20 mM citrate. Additionally, the amount of sucrose may be decreased in the lyophilization formulation to a range from about 0% to about 5% sucrose.

Thickening agents may be added directly to a liquid formulation according to the present invention and then lyophilized. Alternatively, a lyophilized formulation according to the present invention may be reconstituted by adding a suitable diluent, most preferably water having a thickening agent dissolved therein. Such thickened formulations could be administered by spray.

An example of a preferred thickened KGF-2 polypeptide solution according to the present invention comprises a product formed by mixing:

(1) a topically effective amount of a KGF polypeptide, preferably KGF-2 Δ33;
(2) about 10 mM to about 500 mM sodium citrate buffer;
(3) about 0.01 to about 150 mM NaCl;
(4) about 0.75 to about 1.27 mM, preferably about 1 mM EDTA;
(5) about 0.1% to about 7% sucrose or a combination of about 2.0% glycine and about 0.5% sucrose;
(6) about 0.75 to about 1.5% (w/w) carboxy methyl cellulose or about 0.5 to about 1.5% hydroxy propyl methyl cellulose or about 0.25 to about 0.75% hydroxy ethyl cellulose or about 0 to 1% carbomer or any combination thereof.

The a pH of such a formulation is most preferably pH 6.2.

2) Gelling Agents:

Another aspect of the present invention is directed to gel formulations for KGF-2 polypeptides. Gelling agents may be added to injectable formulations of the present invention to provide a formulation that remains liquid at room temperature and solidifies when applied to the surface of the skin (at about 37° C.). Such formulations may be useful for topical applications where controlled release, adhering to the shape of a wound or avoiding run-off may be important. Such gel formulations are employed for topical uses such as wound healing, to treat skin disorders or any other use which could be treated via topical application of KGF-2 pharmaceutical composition.

Gel formulations for KGF-2 polypeptides according to the present invention comprise:

(1) a topically effective amount of a KGF polypeptide;
(2) a buffer;
(3) a pharmaceutically acceptable diluent, preferably water; and
(4) a gel-forming high molecular weight compound.

Viscosity of gel formulations of the present invention may be in a range of about 1 to about 10,000 cps at room temperature, most preferred about 20 to about 100 cps at room temperature. Viscosity is measured using a rotating spindle viscometer.

Gel forming high molecular weight compounds employed in the present invention are typically water-soluble polymers capable of forming a viscous aqueous solution, or non-water soluble, water-swellable polymers (e.g., collagen) that can also form a viscous solution and that gel upon contact with skin.

Useful gel forming high molecular weight compounds may be selected from vinyl polymers, polyoxyethylene-polyoxypropylene copolymers, polysaccharides, proteins, poly(ethylene oxide), acrylamide polymers and derivatives and or salts thereof. Other compounds that can be used to make pharmaceutical gel formulations used in healing wounds can be found in U.S. Pat. No. 5,427,778, which is herein fully incorporated by reference.

Useful vinyl polymers (or substituted polyethylenes) include polyacrylic acid, polymethacrylic acid, polyvinyl pyrrolidone and polyvinyl alcohol. Useful polysaccharides include cellulose derivatives, glycosaminoglycans, agar, pectin, alginic acid, dextran, starch (α-amylose or amylopectin), and chitosan. Useful glycosaminoglycans include hyaluronic acid, chondroitin, chondroitin-4-sulfate, heparan sulfate and heparin. The glycosaminoglycans may be used to enhance wound healing in combination with any other gel forming polymer such as, for example, collagen, gelatin, fibronectin. The acrylamide polymers may be polyacrylamide or polymethacrylamide polymers.

Preferred high molecular weight gel forming compounds are polyoxyethylene-polyoxypropylene block copolymers, especially those block copolymers that are designated in the trade as PLURONICS (BASF) or POLAXAMERS (BASF).

In one preferred embodiment, the gel of the present invention may comprise about 10 to about 60% by weight of a polyoxyethylene-polyoxypropylene block copolymer having an average molecular weight of about 500 to 50,000. In a more preferred embodiment, the gel of the present invention may comprise about 14 to about 18% by weight of block copolymers having a molecular weight in the range 1,000 to 15,000. Preferred block copolymers of the present invention are Pluronic F108 and Pluronic F127.

Polyoxyethylene-polyoxpropylene block copolymers (Pluronic or Poloxamer) have great potential for use in topical drug delivery systems because they exhibit reverse thermal gelation behavior, have good drug release characteristics as well as low toxicity. Gels are formed as the solution is warmed. Thus, the gel is a low viscosity aqueous solution at room temperature but when it contacts the mammalian body and is warmed by body temperature the viscosity increases as the solution gels. Pluronic gels can be used for the controlled delivery of KGF-2 polypeptides to, for example, wounds and other such sites where topical delivery is desirable. KGF-2 polypeptides can be combined with the Pluronic in the liquid state and applied to the wound. Gelation occurs and effectively reduces the rate that the polypeptides are released to the wound and thereby permits prolonged contact between the polypeptides and the wound site. The benefits of using such gel formulations include keeping the wound moist and having a pharmaceutical compound that is form-fitting to the wound or other such site where the compound may be applied.

The preferred gel formulations for KGF-2 polypeptides according to the present invention comprises citrate buffer and a Pluronic. The formulation may comprise an amount of citric acid or a pharmaceutically acceptable salt, thereof.

The gel formulation according to the present invention may also include an chelating agent, a stabilizing amount of antioxidants or thiols. The gel formulation will include a high molecular weight compound, such as a Pluronic, or water-soluble etherified cellulose, and the like in an amount that will form a gel. In the gel formulation according to the present invention, the KGF-2 polypeptides are preferably in a concentration of about 0.01 mg/ml to about 10 mg/ml.

Preferably, the gel formulations are formed by mixing:
(1) a KGF-2 polypeptide, preferably KGF-2 Δ33, in a final calculated concentration of 0.01 mg/ml to about 10 mg/ml;
(2) an effective amount of a buffering agent;
(3) about 10% to about 60%, or more preferably about 14% to about 18% by weight of a polyoxyethylene-polyoxypropylene block copolymer having an average molecular weight of about 500 to 50,000; and
(4) a pharmaceutically acceptable diluent, preferably water.

Another preferred gel formulation comprises:
(1) a pharmaceutically active amount of KGF-2 polypeptide;
(2) about 10 mM to about 500 mM sodium citrate;
(3) about 0.01 mM to about 150 mM NaCl;
(4) about 1 mM EDTA;
(5) about 0.1% to about 7% sucrose or about 2.0% glycine and about 0.5% sucrose;
(6) about 14% to about 18% Pluronic F127; and
(7) water,
wherein the formulation is at a pH of about pH 6.2.

Most preferably, the gel formulation comprises:
(1) a KGF-2 polypeptide, preferably KGF-2 Δ33, at a concentration range of about 0.01 mg/ml to about 10 mg/ml (w/v), more preferably about 0.1 mg/ml to about 3 mg/ml, and most preferably about 0.2 mg/ml;
(2) sodium citrate at a concentration range of about 5 mM to about 20 mM;
(3) about 10% to about 25% (w/v), preferably about 15 to about 25, and most preferably about 16% of Pluronic 127 or Poloxamer 407;
(4) about 6.7% to about 7.3% sucrose, preferably about 7% sucrose or about 2.0% glycine and about 0.5% sucrose; and
(5) water to volume.

The gel formulation optionally further includes one or more of the following:
(6) EDTA at a concentration range of about 0.1 mM to about 10 mM.
(7) NaCl at a concentration range of about 0.01 mM to about 125 mM. The preferred pH ranges for the gel formulation is from about pH 5.0 to about pH 8.0, preferably pH 6.2 and the resulting gel formulation should be isotonic.

3) Additional Stabilizing Agents:
All of the foregoing formulations of the present invention may benefit from anti-oxidants, metal chelating agents, thiol containing compounds and other general stabilizing agents. Examples of such stabilizing agents, include, but are not limited to:
(a) about 0.5% to about 2% w/v glycerol,
(b) about 0.1% to about 1% w/v methionine,
(c) about 0.1% to about 2% w/v monothioglycerol,
(d) about 1 mM to about 10 mM EDTA,
(e) about 0.01% to about 2% w/v ascorbic acid,
(f) 0.003% to about 0.02% w/v polysorbate 80,
(g) 0.001% to about 0.05% w/v polysorbate 20,
(h) arginine, preferably at a concentration of about 0.5% to about 2.5%, most preferably about 1.7%,
(i) heparin or a heparin analog (negatively charged),
(j) dextran sulfate, preferably at a concentration of about 0.5% and 0.05%,
(k) cyclodextrins or sulfated cyclodextrins,
(l) anionic or polyanionic species [heparin analogs],
(m) lysine, preferably at a concentration of 10%,
(n) hydroxypropyl-β-cyclodextrin, preferably at a concentration of about 2 to about 10%,
(o) sulfated-6-cyclodextrin, preferably at a concentration of about 0.1% and 10%, most preferably at about 1%, or
(p) combinations thereof.

Administration of KGF-2 Polypeptides

The KGF-2 polypeptide formulations of the present invention may employ suitable pharmaceutical diluents that are known to be useful in pharmaceutical compositions. Such a diluents include but are not limited to, saline, buffered saline, dextrose, water, glycerol, ethanol, and combinations thereof. The formulation should suit the mode of administration. Preferably, the pharmaceutical compositions will be formulated according to the present invention, as indicated above. Water is a preferred diluent.

The polypeptide having KGF-2 activity may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition, including whether another agent, if any, is employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in *Remington's Pharmaceutical Sciences* (latest edition), Mack Publishing Company, Easton, Pa. The "effective amount" of KGF-2 for purposes herein (including a KGF-2 effective amount) is thus determined by such considerations.

The pharmaceutical compositions of the present invention may be administered in a convenient manner such as by the oral, rectal, topical, intravenous, intraperitoneal, intramuscular, intraarticular, subcutaneous, intranasal, inhalation, intraocular or intradermal routes. Parenteral and topical delivery are the preferred routes of administration. The term "parenteral" as used herein refers to modes of administration which include intravenous, intramuscular, intraperitoneal, intrastemal, subcutaneous and intraarticular injection and infusion.

The pharmaceutical compositions are administered in an amount which is effective for treating and/or prophylaxis of the specific indication. In most cases, the KGF-2 dosage is from about 1 µg/kg to about 30 mg/kg body weight daily, taking into account the routes of administration, symptoms, etc. However, the dosage can be as low as 0.001 µg/kg. For example, in the specific case of topical administration dosages are preferably administered from about 0.01 µg to 9 mg per cm². In the case of intranasal and intraocular administration, dosages are preferably administered from about 0.001 µg/ml to about 10 mg/ml, and more preferably from about 0.05 mg/ml to about 4 mg/ml.

As a general proposition, the total pharmaceutically effective amount of the KGF-2 polypeptide administered parenterally will be in the range of about 1 µg/kg/day to 10 mg/kg/day of patient body weight, although, as noted above, this will be subject to therapeutic discretion. If given continuously, the KGF-2 polypeptide is typically administered at a dose rate of about 1 µg/kg/hour to about 50 µg/kg/hour, either by 1–4 injections per day or by continuous subcutaneous infusions, for example, using a mini-pump. An intravenous bag solution or bottle solution may also be employed.

A course of KGF-2 polypeptide treatment to affect the fibrinolytic system appears to be optimal if continued longer than a certain minimum number of days, 7 days in the case of the mice. The length of treatment needed to observe changes and the interval following treatment for responses to occur appears to vary depending on the desired effect.

For parenteral administration, in one embodiment, the KGF-2 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the KGF-2 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mack Publishing Company, Easton, Pa.

KGF-2 polypeptides may also be administered to the eye to treat lacrimal gland injuries, disorders and pathologies in animals and humans as a liquid, drop, or thickened liquid, a gel.

KGF-2 polypeptides can also be intranasally administered to the nasal mucosa to treat disorders, injuries and pathologies of the nasal mucosa and sinus epithelia in animals and humans as liquid drops or in a spray form.

Generally, the formulations are prepared by contacting the KGF-2 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mack Publishing Company, Easton, Pa.

The carrier may also contain minor amounts of suitable additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

KGF-2 is typically formulated in such vehicles at a concentration of about 0.01 µg/ml to 50 mg/ml, preferably 0.01 µg/ml to 10 mg/ml, at a pH of about 5 to about 8, preferably about 6 to about 7, most preferably about pH 6.2. It will be understood that the use of certain of the foregoing excipients, carriers, or stabilizers will result in the formation of KGF-2 salts.

KGF-2 to be used for therapeutic administration may be sterile. Sterility is readily accomplished by filtration through sterile filtration membranes (e.g., 0.2 micron membranes). Therapeutic KGF-2 compositions may be placed into a container having a sterile access port, for example, an intravenous solution bag or vial having a stopper pierceable by a hypodermic injection needle.

KGF-2 ordinarily will be stored in unit or multi-dose containers, for example, sealed ampules or vials, as an aqueous solution or as a lyophilized formulation for reconstitution. As an example of a lyophilized formulation, 3-ml vials are filled with 1 ml of sterile-filtered 1% (w/v) aqueous KGF-2 solution, and the resulting mixture is lyophilized. The infusion solution is prepared by reconstituting the lyophilized KGF-2 using Water-for-Injection which may optionally include one or more antioxidants.

Dosaging may also be arranged in a patient specific manner to provide a predetermined concentration of an KGF-2 activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

The KGF-2 is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(–)-3-hydroxybutyric acid (EP 133,988). Sustained-release KGF-2 compositions also include liposomally entrapped KGF-2. Liposomes containing KGF-2 are prepared by methods known per se: DE 3,218,121; Epstein, et al., *Proc. Natl. Acad. Sci. USA* 82:3688–3692 (1985); Hwangetal., *Proc. Natl. Acad. Sci. USA* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal KGF-2 therapy.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

When the present inventors examined the biological activity and stability of the KGF-2 polypeptide prepared according to the formulations of the present invention, it was surprisingly discovered that the use of monothioglycerol may stabilize the KGF-2 polypeptides and may behave as a potentiating agent for KGF-2 polypeptides in wound healing. The optimal concentration range for the potentiating effect of the monothioglycerol was 0.1% to 2% w/v.

KGF-2 Polypeptides

KGF-2 stimulates the proliferation of epithelial cells and epidermal keratinocytes but not mesenchymal cells such as fibroblasts. Thus, "a polypeptide having KGF-2 protein-like activity" includes polypeptides that exhibit the KGF-2 activity, in the keratinocyte proliferation assay set forth below and U.S. application Ser. No. 08/910,875, abandoned, and can bind to the FGF receptor isoforms 1-iiib and 2-iiib. Although the degree of activity need not be identical to that of the KGF-2 protein, preferably, "a polypeptide having KGF-2 protein-like activity" exhibits substantially similar activity as compared to the KGF-2 protein (i.e., the candidate polypeptide exhibits greater activity or not more than tenfold less and, preferably, not more than about twofold less activity relative to the reference KGF-2 protein).

The KGF-2 polypeptides used in the formulations of the present invention may or may not have the N-terminal methionine, preferably the polypeptide will be lacking the N-terminal methionine.

The KGF-2 cDNA clone was deposited as ATCC Deposit No. 75977 on Dec. 16, 1994 at the American Type Culture Collection, Patent Depository, 10801 University Blvd., Manassas, Va. 20110–2209. In addition, a cDNA encoding KGF-2 Δ33 inserted into an expression vector, pHE4-5, was deposited at the ATCC on Jan. 9, 1998 as ATCC No. 209575.

The terms "fragment," "derivative" and "analog" when referring to the polypeptide, of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the KGF-2 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

The polypeptides of the present invention are preferably in an isolated form. By "isolated polypeptide" is intended a polypeptide removed from its native environment. Thus, a polypeptide produced and/or contained within a recombinant host cell is considered isolated for purposes of the present invention. Also intended are polypeptides that have been purified, partially or substantially, from a recombinant host cell or a native source.

The pharmaceutical formulations of the present invention include the KGF-2 polypeptide of SEQ ID NO:2 (in particular the mature polypeptide) and deletion mutants thereof, as well as polypeptides which have at least 90%, 95%, 96%, 97%, 98%, 99% similarity (more preferably at least 90%, 95%, 96%, 97%, 98%, 99% identity) to the polypeptide of SEQ ID NO:2 and deletion mutants thereof, and also include portions of such polypeptides with such portion of the polypeptide (such as the deletion mutants described below) generally containing at least 30 amino acids and more preferably at least 50 amino acids.

As known in the art "similarity" between two polypeptides is determined by comparing the amino acid sequence and its conservative amino acid substituted sequence of one polypeptide to the sequence of a second polypeptide.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied*

*Mathematics* 2:482–489, 1981) to find the best segment of similarity between two sequences.

By a polypeptide having an amino acid sequence at least, for example, 95% "identical" to a reference amino acid sequence of a KGF-2 polypeptide is intended that the amino acid sequence of the polypeptide is identical to the reference sequence except that the polypeptide sequence may include up to five amino acid alterations per each 100 amino acids of the reference amino acid of the KGF-2 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 [SEQ ID NO:2] or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

Proteins of the invention may be naturally occurring, produced recombinantly, or can be chemically synthesized using techniques known in the art (e.g., see Creighton, 1983, Proteins: Structures and Molecular Principles, W. H. Freeman & Co., N.Y., and Hunkapiller, M., et al., *Nature* 310:105–111 (1984)). For example, a peptide corresponding to a fragment of the KGF-2 polypeptide of the invention can be synthesized by use of a peptide synthesizer. Furthermore, if desired, nonclassical amino acids or chemical amino acid analogs can be introduced as a substitution or addition into the KGF-2 polypeptide sequence. Non-classical amino acids include, but are not limited to, to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention additionally, encompasses KGF-2 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of KGF-2 which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

KGF-2 Deletion Mutants

Native KGF-2 is relatively unstable in the aqueous state and it undergoes chemical and physical degradation resulting in loss of biological activity during processing and storage. Native KGF-2 is also prone to aggregation in aqueous solution, at elevated temperatures and it becomes inactivated under acidic conditions.

Particularly preferred KGF-2 polypeptides are the deletion mutants shown below (numbering starts with the first amino acid in the protein (Met):

```
Thr (residue 36) -- Ser (residue 208)

Cys (37) -- Ser (208)

Gln (38) -- Ser (208)

Ala (39) -- Ser (208)

Leu (40) -- Ser (208)

Gly (41) -- Ser (208)

Gln (42) -- Ser (208)

Asp (43) -- Ser (208)

Met (44) -- Ser (208)

Val (45) -- Ser (208)

Ser (46) -- Ser (208)
```

-continued

Pro (47) -- Ser (208)

Glu (48) -- Ser (208)

Ala (49) -- Ser (208)

Thr (50) -- Ser (208)

Asn (51) -- Ser (208)

Ser (52) -- Ser (208)

Ser (53) -- Ser (208)

Ser (54) -- Ser (208)

Ser (55) -- Ser (208)

Ser (56) -- Ser (208)

Phe (57) -- Ser (208)

Ser (59) -- Ser (208)

Ser (62) -- Ser (208)

Ala (63) -- Ser (208)

Gly (64) -- Ser (208)

Arg (65) -- Ser (208)

Val (67) -- Ser (208)

Ser (69) -- Ser (208)

Val (77) -- Ser (208)

Arg (80) -- Ser (208)

Met (1), Thr (36), or Cys (37) -- His (207)

Met (1), Thr (36), or Cys (37) -- Val (206)

Met (1), Thr (36), or Cys (37) -- Val (205)

Met (1), Thr (36), or Cys (37) -- Met (204)

Met (1), Thr (36), or Cys (37) -- Pro (203)

Met (1), Thr (36), or Cys (37) -- Leu (202)

Met (1), Thr (36), or Cys (37) -- Phe (201)

Met (1), Thr (36), or Cys (37) -- His (200)

Met (1), Thr (36), or Cys (37) -- Ala (199)

Met (1), Thr (36), or Cys (37) -- Ser (198)

Met (1), Thr (36), or Cys (37) -- Thr (197)

Met (1), Thr (36), or Cys (37) -- Asn (196)

Met (1), Thr (36), or Cys (37) -- Lys (195)

Met (1), Thr (36), or Cys (37) -- Arg (194)

Met (1), Thr (36), or Cys (37) -- Arg (193)

Met (1), Thr (36), or Cys (37) -- Thr (192)

Met (1), Thr (36), or Cys (37) -- Lys (191)

Met (1), Thr (36), or Cys (37) -- Arg (188)

Met (1), Thr (36), or Cys (37) -- Arg (187)

Met (1), Thr (36), or Cys (37) -- Lys (183)

Preferred embodiments include the N-terminal deletions Ala (63)–Ser (208) (KGF-2 Δ28) and Ser (69)–Ser (208) (KGF-2 Δ33). Other preferred N-terminal and C-terminal deletion mutants include: Ala (39)–Ser (208); Pro (47)–Ser (208); Val (77)–Ser (208); Glu (93)–Ser (208); Glu (104)–Ser (208); Val (123)–Ser (208); and Gly (138)–Ser (208). Other preferred C-terminal deletion mutants include: Met (1), Thr (36), or Cys (37)–Lys (153).

Also included by the present invention are deletion mutants having amino acids deleted from both the N-terminus and the C-terminus. Such mutants include all combinations of the N-terminal deletion mutants and C-terminal deletion mutants described above, e.g., Ala (39)–His (200), Met (44)–Arg (193), Ala (63)–Lys (153), Ser (69)–Lys (153), etc. Those combinations can be made using recombinant techniques known to those skilled in the art.

Thus, preferred KGF polypeptides for use in pharmaceutical formulations of the present invention comprise N-terminal deletion mutants, including those comprising the amino acid sequence shown in FIG. 1 (SEQ ID NO:2) except for a deletion of at least the first 38 N-terminal amino acid residues (i.e., a deletion of at least Met (1)–Gln (38)) but not more than the first 147 N-terminal amino acid residues of FIG. 1 (SEQ ID NO:2). Alternatively, the formulation comprises a mutant having a deletion that include at least the first 38 N-terminal amino acid residues (i.e., a deletion of at least Met (1)–Gln (38)) but not more than the first 137 N-terminal amino acid residues of FIG. 1 (SEQ ID NO:2). Alternatively, the formulation comprises a mutant having a deletion that will include at least the first 46 N-terminal amino acid residues but not more than the first 137 N-terminal amino acid residues of FIG. 1 (SEQ ID NO:2). Alternatively, the formulation comprises a mutant having a deletion that will include at least the first 62 N-terminal amino acid residues but not more than the first 137 N-terminal amino acid residues of FIG. 1 (SEQ ID NO:2). Alternatively, the formulation comprises a mutant having a deletion that will include at least the first 68 N-terminal amino acid residues but not more than the first 137 N-terminal amino acid residues of FIG. 1 (SEQ ID NO:2). Alternatively, the formulation comprises a mutant having a deletion that will include at least the first 76 N-terminal amino acid residues but not more than the first 137 N-terminal amino acid residues of FIG. 1 (SEQ ID NO:2). Alternatively, the formulation comprises a mutant having a deletion that will include at least the first 92 N-terminal amino acid residues but not more than the first 137 N-terminal amino acid residues of FIG. 1 (SEQ ID NO:2). Alternatively, the formulation comprises a mutant having a deletion that will include at least the first 103 N-terminal amino acid residues but not more than the first 137 N-terminal amino acid residues of FIG. 1 (SEQ ID NO:2). Alternatively, the formulation comprises a mutant having a deletion that will include at least the first 122 N-terminal amino acid residues but not more than the first 137 N-terminal amino acid residues of FIG. 1 (SEQ ID NO:2).

In addition to a formulation comprising a KGF-2 mutant with the ranges of N-terminal deletion mutants described above, the present invention is also directed to a formulation having all combinations of the above described ranges, e.g., deletions of at least the first 62 N-terminal amino acid residues but not more than the first 68 N-terminal amino acid residues of FIG. 1 (SEQ ID NO:2); deletions of at least the first 62 N-terminal amino acid residues but not more than the first 76 N-terminal amino acid residues of FIG. 1 (SEQ ID NO:2); deletions of at least the first 62 N-terminal amino acid residues but not more than the first 92 N-terminal amino acid residues of FIG. 1 (SEQ ID NO:2); deletions of at least the first 62 N-terminal amino acid residues but not more than the first 103 N-terminal amino acid residues of FIG. 1 (SEQ ID NO:2); deletions of at least the first 68 N-terminal amino acid residues but not more than the first 76 N-terminal amino acid residues of FIG. 1 (SEQ ID NO:2); deletions of at least the first 68 N-terminal amino acid residues but not more than the first 92 N-terminal amino acid residues of FIG. 1 (SEQ ID NO:2); deletions of at least the first 68 N-terminal amino acid residues but not more than the first 103 N-terminal amino acid residues of FIG. 1 (SEQ ID NO:2); deletions of at least the first 46 N-terminal amino acid residues but not more than the first 62 N-terminal amino acid residues of FIG. 1 (SEQ ID NO:2); deletions of at least the first 46 N-terminal amino acid residues but not more than the first 68 N-terminal amino acid residues of FIG. 1 (SEQ ID NO:2); deletions of at least the first 46 N-terminal amino acid residues but not more than the first 76 N-terminal amino acid residues of FIG. 1 (SEQ ID NO:2); etc.

In another embodiment, formulations comprising C-terminal deletion mutants are provided by the present invention. Preferably, the N-terminal amino acid residue of said C-terminal deletion mutants is amino acid residue 1 (Met), 36 (Thr), or 37 (Cys) of FIG. 1 (SEQ ID NO:2). Such formulations comprising mutants include those comprising the amino acid sequence shown in FIG. 1 (SEQ ID NO:2) except for a deletion of at least the last C-terminal amino acid residue (Ser (208)) but not more than the last 55 C-terminal amino acid residues (i.e., a deletion of amino acid residues Glu (154)–Ser (208)) of FIG. 1 (SEQ ID NO:2). Alternatively, the formulation comprises a mutant having a deletion that will include at least the last C-terminal amino acid residue but not more than the last 65 C-terminal amino acid residues of FIG. 1 (SEQ ID NO:2). Alternatively, the formulation comprises a mutant having a deletion that will include at least the last 10 C-terminal amino acid residues but not more than the last 55 C-terminal amino acid residues of FIG. 1 (SEQ ID NO:2). Alternatively, the formulation comprises a mutant having a deletion that will include at least the last 20 C-terminal amino acid residues but not more than the last 55 C-terminal amino acid residues of FIG. 1 (SEQ ID NO:2). Alternatively, the formulation comprises a mutant having a deletion that will include at least the last 30 C-terminal amino acid residues but not more than the last 55 C-terminal amino acid residues of FIG. 1 (SEQ ID NO:2). Alternatively, the formulation comprises a mutant having a deletion that will include at least the last 40 C-terminal amino acid residues but not more than the last 55 C-terminal amino acid residues of FIG. 1 (SEQ ID NO:2). Alternatively, the formulation comprises a mutant having a deletion that will include at least the last 50 C-terminal amino acid residues but not more than the last 55 C-terminal amino acid residues of FIG. 1 (SEQ ID NO:2).

In addition to a formulation comprising a KGF-2 mutant with the ranges of C-terminal deletion mutants described above, the present invention is also directed to a formulation having all combinations of the above described ranges, e.g., deletions of at least the last C-terminal amino acid residue but not more than the last 10 C-terminal amino acid residues of FIG. 1 (SEQ ID NO:2); deletions of at least the last C-terminal amino acid residue but not more than the last 20 C-terminal amino acid residues of FIG. 1 (SEQ ID NO:2); deletions of at least the last C-terminal amino acid residue but not more than the last 30 C-terminal amino acid residues of FIG. 1 (SEQ ID NO:2); deletions of at least the last C-terminal amino acid residue but not more than the last 40 C-terminal amino acid residues of FIG. 1 (SEQ ID NO:2); deletions of at least the last 10 C-terminal amino acid residues but not more than the last 20 C-terminal amino acid residues of FIG. 1 (SEQ ID NO:2); deletions of at least the last 10 C-terminal amino acid residues but not more than the last 30 C-terminal amino acid residues of FIG. 1 (SEQ ID NO:2); deletions of at least the last 10 C-terminal amino acid residues but not more than the last 40 C-terminal amino acid residues of FIG. 1 (SEQ ID NO:2); deletions of at least the last 20 C-terminal amino acid residues but not more than the last 30 C-terminal amino acid residues of FIG. 1 (SEQ ID NO:2); etc.

In yet another embodiment, the KGF-2 polypeptide can be a deletion mutant having amino acids deleted from both the N-terminal and C-terminal residues. Such mutants include all combinations of the N-terminal deletion mutants and C-terminal deletion mutants described above. Such mutants include those comprising the amino acid sequence shown in FIG. 1 (SEQ ID NO:2) except for a deletion of at least the first 46 N-terminal amino acid residues but not more than the first 137 N-terminal amino acid residues of FIG. 1 (SEQ ID NO:2) and a deletion of at least the last C-terminal amino acid residue but not more than the last 55 C-terminal amino acid residues of FIG. 1 (SEQ ID NO:2). Alternatively, a deletion can include at least the first 62, 68, 76, 92, 103, or 122 N-terminal amino acids but not more than the first 137 N-terminal amino acid residues of FIG. 1 (SEQ ID NO:2) and a deletion of at least the last 10, 20, 30, 40, or 50 C-terminal amino acid residues but not more than the last 55 C-terminal amino acid residues of FIG. 1. Further included are all combinations of the above described ranges.

KGF-2 Substitution Mutants

Useful KGF-2 polypeptides include those having substitution of amino acids. Native mature KGF-2 contains 44 charged residues, 32 of which carry a positive charge. Depending on the location of such residues in the protein's three dimensional structure, substitution of one or more of these clustered residues with amino acids carrying a negative charge or a neutral charge may alter the electrostatic interactions of adjacent residues and may be useful to achieve increased stability and reduced aggregation of the protein. Aggregation of proteins cannot only result in a loss of activity but be problematic when preparing pharmaceutical formulations, because they can be immunogenic (Pinckard et al., *Clin. Exp. Immunol.* 2:331–340 (1967), Robbins et al., *Diabetes* 36: 838–845 (1987), Clelandetal., *Crit. Rev. Therapeutic Drug Carrier Systems* 10: 307–377 (1993)). Any modification should give consideration to minimizing charge repulsion in the tertiary structure of the protein molecule. Thus, of special interest are substitutions of charged amino acid with another charge and with neutral or negatively charged amino acids. The latter results in proteins with a reduced positive charge to improve the characteristics of KGF-2. Such improvements include increased stability and reduced aggregation of the analog as compared to the native KGF-2 protein.

The replacement of amino acids can also change the selectivity of binding to cell surface receptors. Ostade et al., *Nature* 361: 266–268 (1993), described certain TNF alpha mutations resulting in selective binding of TNF alpha to only one of the two known TNF receptors.

KGF-2 molecules may include one or more amino acid substitutions, deletions or additions, either from natural mutation or human manipulation. Examples of some preferred mutations are: Ala (49) Gln, Asn (51) Ala, Ser (54) Val, Ala (63) Pro, Gly (64) Glu, Val (67) Thr, Trp (79) Val, Arg (80) Lys, Lys (87) Arg, Tyr (88) Trp, Phe (89) Tyr, Lys

(91) Arg, Ser (99) Lys, Lys (102) Gln, Lys 103(Glu), Glu (104) Met, Asn (105) Lys, Pro (107) Asn, Ser (109) Asn, Leu (111) Met, Thr (114) Arg, Glu(117) Ala, Val (120) Ile, Val (123) Ile, Ala (125) Gly, Ile (126) Val, Asn (127) Glu, Asn (127) Gln, Tyr (130) Phe, Met (134) Thr, Lys (136) Glu, Lys (137) Glu, Gly (142) Ala, Ser (143) Lys, Phe (146) Ser, Asn (148) Glu, Lys (151) Asn, Leu (152) Phe, Glu (154) Gly, Glu (154) Asp, Arg (155) Leu, Glu (157) Leu, Gly (160) His, Phe (167) Ala, Asn (168) Lys, Gln (170) Thr, Arg(174) Gly, Tyr(177) Phe, Gly (182) Gln, Ala (185)Val, Ala (185) Leu, Ala (185) Ile, Arg (187) Gln (190) Lys, Lys (195) Glu, Thr (197) Lys, Ser (198) Thr, Arg (194) Glu, Arg (194) Gln, Lys (191) Glu, Lys( 191)Gln, Arg(1 88) Glu, Arg (188) Gln, Lys (183) Glu.

By the designation, for example, Ala (49) Gln is intended that the Ala at position 49 of FIG. 1 (SEQ ID NO:2) is replaced by Gln.

Changes are preferably of minor nature, such as conservative amino acid substitutions that do not significantly affect the folding or activity of the protein. Examples of conservative amino acid substitutions known to those skilled in the art are set forth below:

| Aromatic: | phenylalanine |
| --- | --- |
|  | tryptophan |
|  | tyrosine |
| Hydrophobic: | leucine |
|  | isoleucine |
|  | valine |
| Polar: | glutamine |
|  | asparagine |
| Basic: | arginine |
|  | lysine |
|  | histidine |
| Acidic: | aspartic acid |
|  | glutamic acid |
| Small: | alanine |
|  | serine |
|  | threonine |
|  | methionine |
|  | glycine |

Of course, the number of amino acid substitutions a skilled artisan would make depends on many factors, including those described above. Generally speaking, the number of substitutions for any given KGF-2 polypeptide will not be more than 50, 40, 30, 20, 10, 5, or 3, depending on the objective. For example, a number of substitutions that can be made in the C-terminus of KGF-2 to improve stability.

Amino acids in KGF-2 that are essential for function can be identified by methods well known in the art, such as site-directed mutagenesis or alanine-scanning mutagenesis (Cunningham and Wells, *Science* 244:1081–1085 (1989). The latter procedure introduces single alanine mutations at every residue in the molecule. The resulting mutant molecules are then tested for biological activity such as receptor binding or in vitro and in vivo proliferative activity. (See, e.g., Example 1). Sites that are critical for ligand-receptor binding can also be determined by structural analysis such as crystallization, nuclear magnetic resonance or photoaffinity labelling. (See for example: Smith et al., *J. Mol. Biol.*, 224: 899–904 (1992); and de Vos et al. *Science*, 255: 306–312 (1992).)

Other useful KGF polypeptides include polypeptides having substitutions of serine for cysteine at amino acid positions 37 and 106 and 150. An uneven number of cysteines means that at least one cysteine residue is available for intermolecular crosslinks or bonds that can cause the protein to adopt an undesirable tertiary structure. Novel KGF-2 proteins that have one or more cysteines replaced by serine or e.g. alanine are generally purified at a higher yield of soluble, correctly folded protein. Although not wishing to be bound by theory, it is believed that the cysteine residue at position 106 is important for function. This cysteine residue is highly conserved among all other FGF family members.

Further KGF-2 polypeptides are described in PCT/US95/01790, filed Feb. 14, 1995, abandoned, and U.S. application Ser. No. 08/461,195, filed Jun. 5, 1995, abandoned, U.S. application Ser. No. 08/696,135, filed Aug. 13,1996, abandoned, U.S. application Ser. No. 60/023,852, filed Aug. 13,1996, abandoned, U.S. application Ser. No. 60/039,045, filed Feb. 28,1997, abandoned, U.S. application Ser. No. 08/862,432, filed May 23, 1997, abandoned, U.S. application Ser. No. 60/055,561, filed Aug. 13, 1997, abandoned, U.S. application Ser. No. 08/910, 875, filed Aug. 13,1997, abandoned, U.S. application Ser. No. 09/023,082, filed Feb. 13, 1998, now U.S. Pat. No. 6,077,692, issued Jun. 20, 2000, U.S. application Ser. No. 09/345,373, filed Jul. 1, 1999, pending, U.S. application Ser. No. 60/142,343, filed Jul. 2, 1999, abandoned, U.S. application Ser. No. 60/143,648, filed Jul. 14, 1999, abandoned, U.S. application Ser. No. 60/144,024, filed Jul. 15, 1999, abandoned, U.S. application Ser. No. 60/148,628, filed Aug. 12, 1999, abandoned, U.S. application Ser. No. 60/149,935, filed Sep. 24, 1999, abandoned, U.S. application Ser. No. 60/163,375, filed Nov. 3,1999, abandoned, U.S. application Ser. No. 60/171,677, filed Dec. 22, 1999, abandoned, and U.S. application Ser. No. 60/198,322, filed Apr. 19, 2000, abandoned, the disclosures of all of which are incorporated by reference herein.

Therapeutic Uses of KGF-2 Polypeptide Compositions

The polypeptides of the present invention may stimulate keratinocyte cell growth and proliferation. Accordingly, compositions of the present invention can be employed to stimulate epithelial cell proliferation and basal keratinocytes for the purpose of wound healing, and to stimulate hair follicle production and healing of dermal wounds. These wounds may be of superficial nature or may be deep and involve damage of the dermis and the epidermis of skin.

KGF-2 is useful for treating a number of diseases and conditions. For example, KGF-2 is active in vitro and in vivo in various wound healing models. See, U.S. application Ser. Nos. 08/910, 875, filed Aug. 13, 1997, abandoned, and U.S. application Ser. No. 09/023,082 filed Feb. 13, 1998, now U.S. Pat. No. 6,077,692, issued Jun. 20, 2000.

The individual to which KGF-2 is administered may heal wounds at a normal rate or may be healing impaired. When administered to an individual who is not healing impaired, KGF-2 is administered to accelerate the normal healing process. When administered to an individual who is healing impaired, KGF-2 is administered to facilitate the healing of wounds which would otherwise heal slowly or not at all. A number of afflictions and conditions can result in healing impairment. These afflictions and conditions include diabetes (e.g., Type II diabetes mellitus), treatment with both steroids and non-steroid pharmacological agents, and ischemic blockage or injury.

A number of growth factors have been shown to promote wound healing in healing impaired individuals. These growth factors include growth hormone-releasing factor, platelet-derived growth factor, and basic fibroblast growth factors. Thus, the present invention also encompasses the administration of KGF-2 compositions in conjunction with one or more additional growth factors or other agent which promotes wound healing.

The compositions of the present invention also promote the healing of anastomotic and other wounds caused by surgical procedures in individuals which both heal wounds at a normal rate and are healing impaired.

The compositions of the present invention may also be employed to stimulate differentiation of cells, for example muscle cells, cells which make up nervous tissue, prostate cells, and lung cells.

The compositions of the present invention are clinically useful in stimulating wound healing of wounds including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, and burns resulting from heat exposure to extreme temperatures of heat or cold, or exposure to chemicals, in normal individuals and those subject to conditions which induce abnormal wound healing such as uremia, malnutrition, vitamin deficiencies, obesity, infection, immunosuppression and complications associated with systemic treatment with steroids, radiation therapy, and antineoplastic drugs and antimetabolites. The compositions are also useful for promoting the healing of wounds associated with ischemia and ischemic injury, e.g., chronic venous leg ulcers caused by an impairment of venous circulatory system return and/or insufficiency; for promoting dermal reestablishment subsequent to dermal loss; increasing the tensile strength of epidermis and epidermal thickness; and increasing the adherence of skin grafts to a wound bed and to stimulate re-epithelialization from the wound bed.

Other therapeutic uses for the KGF-2 polypeptides include, but are not limited to, for example, to stimulate epithelial cell proliferation and basal keratinocytes for the purpose of treating burns and skin defects such as psoriasis and epidermolysis bullosa. KGF-2 can be used to increase the adherence of skin grafts to a wound bed and to stimulate re-epithelialization from the wound bed. KGF-2 can also be used to reduce the side effects of gut toxicity that result from radiation, chemotherapy treatments or viral infections. KGF-2 can be used to treat diseases and conditions of the liver, lung, kidney, breast, pancreas, stomach, small intestine, and large intestine. KGF-2 can be used to treat inflamamatory bowel diseases, diabetes, thrombocytopenia, hypofibrinogenemia, hypoalbuminemia, hypoglobulinemia, hemorrhagic cystitis, xerostomia, keratoconjunctivitis sicca. KGF-2 can be used to stimulate the epithelial cells of the salivary glands, lacrimal glands and stimulating re-epithelialization of the sinuses and the growth of nasal mucosa.

A number of other indications that can be treated by the composition of the present invention are described in U.S. application Ser. No. 08/910, 875, abandoned, and U.S. application Ser. No. 09/023,082, now U.S. Pat. No. 6,077, 692, issued Jun. 20, 2000, and are herein incorporated by reference.

The present invention is directed to novel liquid and lyophilized formulations of KGF-2 and deletion mutants thereof. This invention further relates to formulations of KGF-2 for therapeutic use. The formulations provide superior stability to the active KGF-2 polypeptides and in some instances, potentiate and dramatically increase the wound-healing activity of the polypeptides.

As used herein, by "individual" is intended an animal, preferably a mammal (such as apes, cows, horses, pigs, boars, sheep, rodents, goats, dogs, cats, chickens, monkeys, rabbits, ferrets, whales, and dolphins), and more preferably a human.

The KGF-2 Δ33 polypeptide used in the formulations of the present invention may or may not have the N-terminal methionine, preferably the polypeptide will be lacking the N-terminal methionine. Stability of the KGF-2 polypeptide formulations of the present invention is determined by proliferation assays, as described herein below.

Other therapeutic uses of KGF-2 are described in U.S. application Ser. No. 60/074,585, filed Feb. 13, 1998, abandoned, U.S. application Ser. No. 60/114,484, filed Dec. 30, 1998, abandoned, and U.S. application Ser. No. 09/248, 998, filed Feb. 12, 1999, pending, the disclosures of all of which are incorporated by reference herein.

Keratinocyte Proliferation Assays

Dermal keratinocytes are cells in the epidermis of the skin. The growth and spreading of keratinocytes in the skin is an important process in wound healing. A proliferation assay of keratinocyte is therefore a valuable indicator of protein activities in stimulating keratinocyte growth and consequently, wound healing.

Keratinocytes are, however, difficult to grow in vitro. Few keratinocyte cell lines exist. These cell lines have different cellular and genetic defects. In order to avoid complications of this assay by cellular defects such as loss of key growth factor receptors or dependence of key growth factors for growth, primary dermal keratinocytes are chosen for this assay. These primary keratinocytes are obtained from Clonetics, Inc. (San Diego, Calif.).

The bioactivity of KGF-2 polypeptides can be determined by a cell proliferation assay employing murine Baf3 2b cells that have been transfected with the fibroblast growth factor 2iiib receptor (FGFR2iiib). Proliferation of the cells is measured by the incorporation of [Methyl-$^3$H]-thymidine after the cells have been exposed to the protein as described below. The assay is carried out in a 96 well tissue culture cluster plate with about 22,000 Baf3 2b cells in each well. The cells are exposed to different concentrations of a KGF-2 polypeptide in triplicate and incubated at 37° C. in a $CO_2$ incubator for approximately 48 hours. An approximate amount of cell media containing labelled thymidine is subsequently added into each well and the incubation is continued for another 5 hours. The cells are then harvested on a glass fiber filter mat, in the 96 well format, using a cell harvester. The filter mats are dried and radioactivity incorporated into each sample is counted using a flat-bed liquid scintillation counter. Under these assay conditions, cells exposed to KGF-2 show an increased incorporation of radioactivity compared to control cells that have been treated either with an appropriate dilution of the placebo buffer or simply with phosphate buffered saline.

Another useful keratinocyte proliferation assay is with Alamar Blue. Alamar Blue is a viable blue dye that is metabolized by the mitochondria when added to the culture media. The dye then turns red in tissue culture supernatants. The amounts of the red dye may be directly quantitated by reading difference in optical densities between 570 nm and 600 nm. This reading reflects cellular activities and cell number.

Normal primary dermal keratinocytes (CC-0255, NHEK-Neo pooled) are purchased from Clonetics, Inc. These cells are passage 2. Keratinocytes are grown in complete keratinocyte growth media (CC-3001, KGM; Clonetics, Inc.) until they reach 80% confluency. The cells are trypsinized according to the manufacturer's specification. Briefly, cells are washed twice with Hank's balanced salt solution. 2–3 ml of trypsin is added to cells for about 3–5 min at room temperature. Trypsin neutralization solution is added and cells are collected. Cells are spun at 600 ×g for 5 min at room temperature and plated into new flasks at 3,000 cells per square centimeter using pre-warmed media.

For the proliferation assay, plate 1,000–2,000 keratinocytes per well of the Corning flat bottom 96-well plates in complete media except for the outermost rows. Fill the outer wells with 200 μl of sterile water. This helps to keep temperature and moisture fluctuations of the wells to the minimum. Grow cells overnight at 37° C. with 5% $CO_2$. Wash cells twice with keratinocyte basal media (CC-3101, KBM, Clonetics, Inc.) and add 100 μl of KBM into each well. Incubate for 24 hours. Dilute growth factors in KBM in serial dilution and add 100 μl to each well. Use KGM as a positive control and KBM as a negative control. Six wells are used for each concentration point. Incubate for two to three days. At the end of incubation, wash cells once with KBM and add 100 μl of KBM with 10% v/v Alamar Blue pre-mixed in the media. Incubate for 6 to 16 hours until media color starts to turn red in the KGM positive control. Measure O.D. 570 nm minus O.D. 600 nm by directly placing plates in the plate reader.

Construction of KGF-2 Deletion Mutants

Useful deletion mutants for use in compositions of the present invention can be constructed by the following protocol.

Deletion mutants were constructed from the 5' terminus and 3 ' terminus of KGF-2 gene using an optimized KGF-2 construct as a template. The deletions were selected based on regions of the gene that might negatively affect expression in E. coli. For the 5' deletion the primers listed below were used as the 5' primer. These primers contain the indicated restriction site and an ATG to code for the initiator methionine. The KGF-2 (FGF-12) 208 amino acid 3' HindIII primer was used for the 3' primer. PCR amplification for 25 rounds was performed using standard conditions. The products for the KGF-2 36aa/208aa deletion mutant were restricted BspHI for the 5' site and HindIII for the 3' site and cloned into the pQE60 which has bee digested with BspHI and HindIII. All other products were restricted with NcoI for the 5' restriction enzyme and HindIII for the 3' site, and cloned into the pQE60 which had been digested with NcoI and HindIII. For KGF-2 (FGF-12), 36aa/ 153 aa and 128aa 3' HindIII was used as the 3'primer with FGF-12 36aa/208aa as the 5' primer. For FGF-12 62aa/153aa, 128aa 3' HindIII was used as the 3' primer with FGF-12 62aa/208aa as the 5' primer. The nomenclature of the resulting clones indicates the first and last amino acid of the polypeptide that results from the deletion. For example, KGF-2 36aa/153aa indicates that the first amino acid of the deletion mutant is amino acid 36 and the last amino acid is amino acid 153 of KGF-2. The construction of these KGF-2 deletion mutants are also described in U.S. application Ser. No. 08/910, 875, abandoned, and U.S. application Ser. No. 09/023,082, now U.S. Pat. No. 6,077,692, issued Jun. 20, 2000, and are herein incorporated by reference. Further, as indicated in below, each mutant has N-terminal Met added thereto. However, the KGF-2 deletion polypeptides used in the formulations according to the present invention may or may not have the N-terminal methionine, preferably the polypeptide will be lacking the N-terminal methionine.

Sequences of the Deletion Primers:

FGF12 36aa/208aa:
  5' BsphI GGACCCTCATGACCTGCCAG-GCTCTGGGTCAGGAC (SEQ ID NO:3)

FGF12 63aa/208aa:
  5' NcoI GGACAGCCATGGCTGGTCGTCACGTTCG (SEQ ID NO:4)

FGF12 77aa/208aa:
  5' NcoI GGACAGCCATGGTTCGTTGGCGTAAACTG (SEQ ID NO:5)

FGF12 93aa/208aa:
  5' NcoI GGACAGCCATGGAAAAAACGG-TAAAGTTTC (SEQ ID NO:6)

FGF12 104aa/208aa:
  5' NcoI GGACCCCCATGGAGAACTGCCCGTAGAGC (SEQ ID NO:7)

FGF12 123aa/208aa:
  5' NcoI GGACCCCCATGGTCAAAGCCATTAACAG-CAAC (SEQ ID NO:8)

FGF12 138aa/208aa:
  5' NcoI GGACCCCCATGGGGAAACTCTATGGCT-CAAAAG (SEQ ID NO:9)

FGF12 3' HindIII: (Used for all above deletion clones)
  CTGCCCAAGCTTATTATGAGTGTACCAC-CATTGGAAG (SEQ ID NO: 10)

FGF12 36aa/153aa:
  5' BsphI (as above)
  3' HindIII CTGCCCAAGCTTATTACTTCAGCTTA-CAGTCATTGT (SEQ ID NO: )

FGF12 63aa/153aa:
  5' NcoI and 3' HindIII, as above.

Construction of N-terminal deletion mutant KGF-2 Δ33

Construction of KGF-2 Δ33 in pQE6

To permit Polymerase Chain Reaction directed amplification and sub-cloning of KGF2 Δ33 into the E. coli protein expression vector, pQE6, two oligonucleotide primers (5952 and 19138) complementary to the desired region of KGF2 were synthesized with the following base sequence.

Primer 5952: 5' GCGGCACATGTCTTACAACCACCT-GCAGGGTG 3' (SEQ ID NO:12)

Primer 19138: 5' GGGCCCAAGCTTATGAGTGTAC-CACCAT 3' (SEQ ID NO:13)

In the case of the N-terminal primer (5952), an AflIII restriction site was incorporated, while in the case of the C-terminal primer (19138) a HindIII restriction site was incorporated. Primer 5952 also contains an ATG sequence adjacent and in frame with the KGF2 coding region to allow translation of the cloned fragment in E. coli, while primer 19138 contains two stop codons (preferentially utilized in E. coli) adjacent and in frame with the KGF2 coding region which ensures correct translational termination in E. coli.

The Polymerase Chain Reaction was performed using standard conditions well known to those skilled in the art and the nucleotide sequence for the mature KGF-2 (aa 36-208) as template. The resulting amplicon was restriction digested with AflIII and HindIII and subcloned into NcoI/HindIII digested pQE6 protein expression vector.

Construction of KGF-2 Δ33 in pHE1

To permit Polymerase Chain Reaction directed amplification and subcloning of KGF2 Δ33 into the E. coli expression vector, pHE1, two oligonucleotide primers (6153 and 6150) corresponding to the desired region of KGF2 were synthesized with the following base sequence.

Primer 6153:5' CCGGCGGATCCCATATGTCTTA-CAACCACCTGCAGG3' (SEQ ID NO:14)

Primer 6150:5' CCGGCGGTACCTTATTATGAGTG-TACCACCATTGG3' (SEQ ID NO:15)

In the case of the N-terminal primer (6153), an NdeI restriction site was incorporated, while in the case of the C-terminal primer (6150) an Asp718 restriction site was incorporated. Primer 6153 also contains an ATG sequence adjacent and in frame with the KGF2 coding region to allow translation of the cloned fragment in E. coli, while primer 6150 contains two stop codons (preferentially utilized in *E. coli*) adjacent and in frame with the KGF2 coding region which ensures correct translational termination in *E. coli*.

The Polymerase Chain Reaction was performed using standard conditions well known to those skilled in the art and the nucleotide sequence for the mature KGF-2 (aa 36-208) as template. The resulting amplicon was restriction digested with NdeI and Asp718 and subcloned into NdeI/Asp718 digested pHE1 protein expression vector.

Nucleotide Sequence of KGF-2 Δ33
ATGTCTTACAACCACCTGCAGGGTGACGTTCGTTGGCGTAAACTGT TCTCTTTCACCAAATACTTCCTGAAAATCGAAAA AAACGGTAAAGTTTCTGGGACCAAGAAGGAGAACTGCCCGTACAG CATCCTGGAGATAACATCAGTAGAAATCGGAGTTG TTGCCGTCAAAGCCATTAACAGCAACTATTACTTAGCCATGAACAA GAAGGGGAAACTCTATGGCTCAAAAGAATTTAAC AATGACTGTAAGCTGAAGGAGAGGATAGAGGAAAATGGATACAAT ACCTATGCATCATTTAACTGGCAGCATAATGGGAG GCAAATGTATGTGGCATTGAATGGAAAAGGAGCTCCAAGG AGAGGACAGAAAACACGAAGGAAAAACACCTCTGCTCACTTTCTT CCAATGGTGGTACACTCATAA (SEQ ID NO:16)

Amino Acid Sequence of KGF-2 Δ33:
MSYNHLQGDVRWRKLFSFTKYFLKIEKNGKVSGTKKENCPYSILEITS VEIGVVAVKAINSNYYLAMNKKGKLYGSKEFNNDCKLKERIEENGYN TYASFNWQHNGRQMYVALNGKGAPRRGQKTRRKNTSAHFLPMVVHS (SEQ ID NO:17)

B. Construction of an Optimized KGF-2 Δ33 Polynucleotide Sequence

In order to increase the expression levels of KGF2 Δ33 in *E. coli*, the codons of the complete gene were optimized to match those most highly used in *E. coli*. As the template utilized to generate the KGF2 Δ33 was codon optimized within the N-terminal region, the C-terminal amino acids (84–208) required optimization.

Firstly, amino acids 172–208 were codon optimized to generate KGF2 Δ33(s172–208). This was achieved by an overlapping PCR strategy. Oligonucleotides PM07 and PM08 (corresponding to amino acids 172–208) were combined and annealed together by heating them to 70° C. and allowing them to cool to 37° C. The annealed oligonucleotides were then utilized as template for a standard PCR reaction which was directed by primers PM09 and PM10. In a separate PCR reaction following standard conditions well known to those skilled in the art and using KGF2 Δ33 as template, oligonucleotides PM05 (which overlaps with the Pst1 site within coding region of KGF2) and PM11 were used to amplify the region of KGF2 corresponding to amino acids 84–172. In a third PCR reaction, the product of the first PCR reaction (corresponding to codon optimized amino acids 172–208) and the product of the second PCR reaction (corresponding to codon non-optimized amino acids 84–172) were combined and used as template for a standard PCR reaction directed by oligonucleotides PM05 and PM10. The resulting amplicon was digested with Pst1/HindIII and sub-cloned into Pst1/HindIII digested pQE6KGF2 Δ33, effectively substituting the corresponding non codon optimized region, and creating pQE6KGF2 Δ33(s 172–208).

To complete the codon optimization of KGF2, a synthetic gene codon optimized for the region of KGF2 corresponding to amino acids 84–172 was generated utilizing overlapping oligonucleotides. Four oligonucleotides (PM31, PM32, PM33 and PM34) were combined and seven cycles of the following PCR was performed: 94° C., 30 secs; 46.5° C., 30 secs; and 72° C., 30 secs.

A second PCR reaction directed by primers PM35 and PM36 was then performed following standard procedures, utilizing 1 μl of the first PCR reaction as template. The resulting codon optimized gene fragment was then digested with Pst1/Sal1 and subcloned into Pst1/Sal1 digested pQE6KGF2 Δ33(s172–208) to create a fully optimized KGF2 encoding gene, pQE6KGF2 Δ33s.

To create an alternative *E. coli* protein expression vector, KGF2 Δ33s was PCR amplified utilising primers PM102 and PM130 on pQE6KGF2 Δ33s. The resulting amplicon was digested with NdeI and EcoRV and subcloned into the pHE1 expression vector which had been digested with NdeI and Asp718 (blunt ended) to create pHEIA33s.

Oligonucleotide Sequences used in construction of codon optimized KGF-2 Δ33s:

PM05: CAACCACCTGCAGGGTGACG (SEQ ID NO:18)

PM07: AACGGTCGACAAATGTATGTGGCACTGAACGGTAAAGGTG CTCCACGTCGTGGTCAGAAAACCCGTCGTAAAAACACC (SEQ ID NO:19)

PM08: GGGCCCAAGCTTAAGAGTGTACCACCATTGGCAGAAAGT GAGCAGAGGTGTTTTTACGACGGGTTTTCTGACCACG (SEQ ID NO:20)

PM09: GCCACATACATTTGTCGACCGTT (SEQID NO:21)

PM10: GGGCCCAAGCTTAAGAGTG (SEQID NO:22)

PM11: GCCACATACATTTGTCGACCGTT (SEQ ID NO:23)

PM31: CTGCAGGGTGACGTTCGTTGGCGTAAACTGTTCTCCTTCACC AAATACTTCCTGAAAATCGAAAAAAACGGTAAAGTTTCTGGTACCA AG (SEQ ID NO:24)

PM32: AGCTTTAACAGCAACAACACCGATTCAACGGAGGTGATTTC CAGGATGGAGTACGGGCAGTTTTCTTTCTTGGTACCAGAAACTTTA CC (SEQ ID NO:25)

PM33: GGTGTTGTTGCTGTTAAAGCTATCAACTCCAACTACTACCTG GCTATGAACAAGAAAGGTAAACTGTACGGTTCCAAAGAATTTAAC AAC (SEQ ID NO:26)

PM34: GTCGACCGTTGTGCTGCCAGTTGAAGGAAGCGTAGGTGTTGT AACCGTTTTCTTCGATACGTTCTTTCAGTTTACAGTCGTTGTTAAAT TCTTTGGAACC (SEQ ID NO:27)

PM35: GCGGCGTCGACCGTTGTGCTGCCAG (SEQ ID NO:28)

PM36: GCGGCCTGCAGGGTGACGTTCGTTGG (SEQ ID NO:29)

PM102: CCGGCGGATCCCATATGTCTTACAACCACCTGCAGG (SEQ ID NO:30)

PM130: CGCGCGATATCTTATTAAGAGTGTACCACCATTG (SEQ ID NO:31)

Nucleotide Sequence of KGF-2 Δ33(s172–208):
ATGTCTTACAACCACCTGCAGGGTGACGTTCGTTGGCGTAAACTGT TCTCCTTCACCAAATACTTCCTGAAAATCGAAAAAAACGGTAAAGT TTCTGGTACCAAGAAAGAAAACTGCCCGTACTCCATCCTGGAAATC ACCTCCGTTGAAATCGGTGTTGTTGCTGTTAAAGCTATCAACTCCA ACTACTACCTGGCTATGAACAAGAAAGGTAAACTGTACGGTTCCAA AGAATTTAACAACGACTGTAAACTGAAA-
GAACGTATCGAAGAAAA CGGTTACAAC-
ACCTACGCTTCCTTCAACTGGCAGCACAAC-
GGTCGA CAAATGTATGTGGCACTGAACGG-
TAAAGGTGCTCCACGTCGTGGTC AGAAAA-
CCCGTCGTAAAAACACCTCTGCTCACTTTC-
TGCCAATGGT GGTACACTCTTAA (SEQ ID
NO:32)

Amino Acid Sequence of KGF-2 Δ33(s172–208):

MSYNHLQGDVRWRKLFSFTKYFLKIEKNGKV-
SGTKKENCPYSILEITS VEIGVVAVKAINSNYY-
LAMNKKGKLYGSKEFNNDCKLKERIEENGYN
TYASFNWQHNGRQMYVALNGKGAPRRGQKT-
RRKNTSAHFLPMVVHS (SEQ ID NO:33)

EXAMPLES

Example 1

KGF-2 Liquid Formulation

The following ingredients were mixed to create a liquid KGF-2 Δ33 formulation is a liquid that is stored at −20° C.

2 mg/ml KGF-2 Δ33 polypeptide, 20 mM sodium acetate, 125 mM sodium chloride, 1 mM EDTA, Water, pH 6.2.

Figure 3:
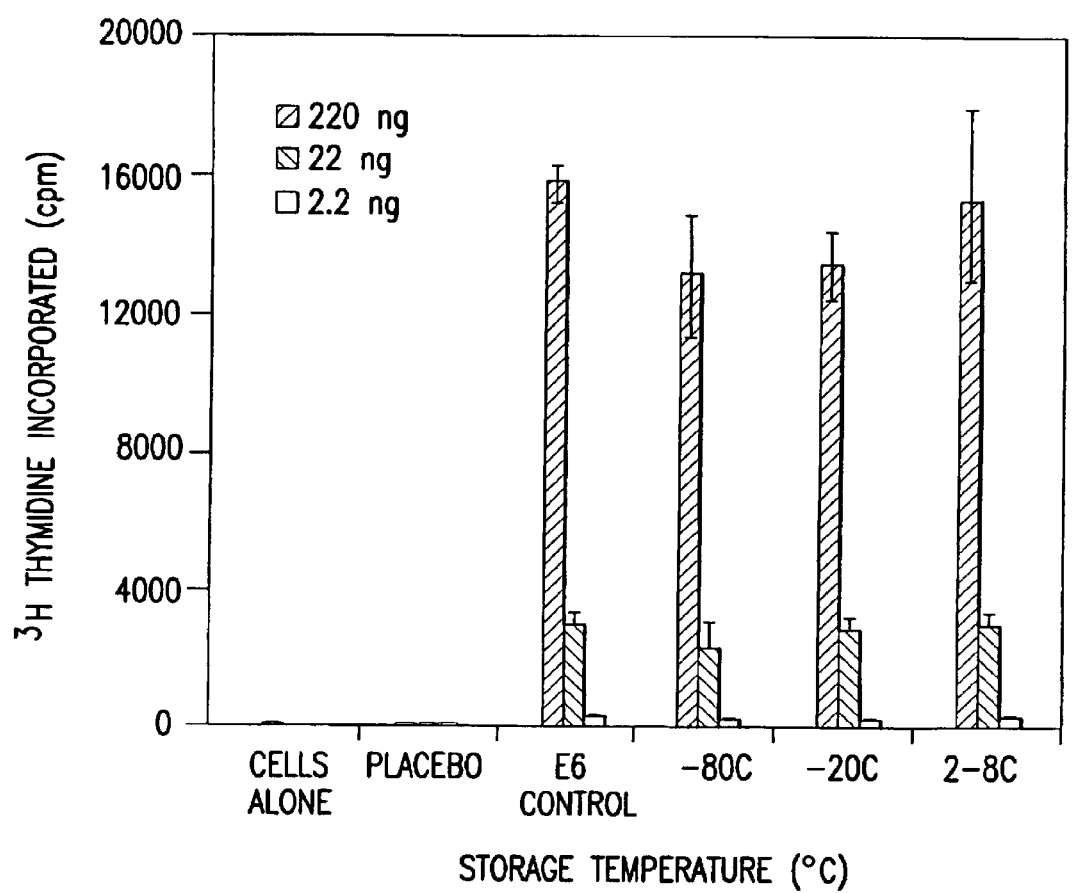
FIG. 3 shows bioactivity results for KGF-2 Δ33 liquid formulation, 10 month stability.

This formulation retained its in vitro bioactivity for up to 10 months at storage conditions at or below 2 to 8° C. The bioactivity at 10 months is shown in FIG. 3. This formulation retained all its physico-chemical properties for up to 11 months at storage conditions at or below Bioactivity was measured using a cell proliferation assay as follows. BaF3 cells, were routinely grown and maintained in RPMI 1640 medium containing 10% NBCS, 10% WEHI cell conditioned medium, 2 mM glutamine, 600 μg/ml GENETICIN, 1 μl β mercaptoethanol/500 ml growth medium, 50 units penicillin and 50 μg/ml streptomycin (Omitz, D., M. et al (1996) J. Biol. Chem. 271:15292–15297). For cell proliferation assays, BaF3 cells were harvested by centrifugation and washed with Basal medium (this has the same composition as the growth medium, but contains no WEHI conditioned medium and is supplemented with 1 μg/ml heparin). Following this operation the cells were resuspended in basal medium and 22,000 cells/180 μl were plated/well in a 96 well cell culture cluster dish. Appropriate dilutions (10× higher than the required final concentration) of KGF 2 were made in PBS in another 96 well plate and added to the cells to a final volume of 200 μl. The cell plates were incubated in a 37° C., 5% $CO_2$ incubator for 36–40 hr. and 0.5 μCi methyl-$^3$H thymidine in 50 μl basal medium was added to each well. The plates were incubated for another 5 hr. in the incubator and cells were harvested by filtration on a glass fiber filter using a Tomtec Harvester 96. Incorporated thymidine was counted on a Wallac β plate scintillation counter.

Example 2

KGF-2 Lyophilized Formulation

The following ingredients were mixed to create a KGF-2 Δ33 lyophilized formulation.

10 mg/ml KGF-2 Δ33, 10 mM sodium citrate, 20 mM sodium chloride, 1 mM EDTA,

7% w/v sucrose, water (removed upon lyophiliztion)

pH6.2.

This formulation retained its in vitro bioactivity for up to 9 months at storage conditions at or below 45° C. The bioactivity at 9 months is shown in FIG. 4. Bioactivity was measured using the cell proliferation assay detailed in Example 1. Reverse-phase HPLC demonstrated that the formulation retained its physio-chemical properties for up to 8 months at temperatures of at or below 45° C. and 75% relative humidity.

Example 3

KGF-2 in a Thickened Formulation

The following ingredients were mixed to create a KGF-2 Δ33 thickened formulation.

2 mg/ml KGF-2 Δ33, 10 mM sodium citrate, 20 mM sodium chloride, 1 mM EDTA,

7% w/v sucrose, 1.25% carboxy methyl cellulose, water pH 6.2.

This formulation is prepared by adding KGF-2 Δ33 polypeptide to the carboxy methyl cellulose solution. The viscosity of the resulting formulation was about 250 cps as determined by rotating spindle viscometer. The KGF-2 polypeptide retained bioactivity in the presence of carboxy methyl cellulose. Bioactivity of the formulation was assayed using the cell proliferation assay detailed in Example 1.

Example 4

KGF-2 in a Gel Formulation

The following ingredients were mixed to create a KGF-2 Δ33 gel formulation.

2 mg/ml KGF-2 Δ33, 10 mM sodium citrate, 20 mM sodium chloride, 1 mM EDTA,

7% w/v sucrose,

16% Pluronic F127, water pH 6.2.

KGF-2 Δ33 is added to a Pluronic solution at about 2° C. to about 8° C. The viscosity of the resulting formulation was about 50 cps at 20° C. and solid at about 37° C. KGF-2 retained bioactivity in the presence of Pluronic F127 as measured by the cell proliferation assay detailed in Example 1.

Example 5

Activation of KGF 2 by Monothioglycerol

KGF-2 Δ33 protein stock formulations (0.1 to 2.0 mg/ml) were prepared with or without monothioglycerol (MTG).

The protein formulations were diluted in 1×phosphate buffered saline (PBS) at pH 7.2 to attain the required concentrations for use in the cell proliferation assays.

Cell Culture

BaF32b cells, were routinely grown and maintained in RPMI 1640 medium containing 10% NBCS, 10% WEHI cell conditioned medium, 2 mM glutamine, 600 μg/ml GENETICIN, 1 μl β mercaptoethanol/500 ml growth medium, 50 units penicillin and 50 μg/ml streptomycin (Ornitz, D., M. et al (1996) *J. Biol. Chem.* 271:15292–15297).

Cell Proliferation Assays

For cell proliferation assays, BaF32b cells were harvested by centrifugation and washed with Basal medium (this has the same composition as the growth medium, but contains no WEHI conditioned medium and is supplemented with 1 μg/ml heparin). Following this operation the cells were resuspended in basal medium and 22,000 cells/180 μl were plated/well in a 96 well cell culture cluster dish. Appropriate dilutions (10×higher than the required final concentration) of KGF 2 were made in PBS in another 96 well plate and added to the cells to a final volume of 200 μl. The cell plates were incubated in a 37° C., 5% $CO_2$ incubator for 36–40 hr. and 0.5 μCi methyl-$^3$H thymidine in 50 μl basal medium was added to each well. The plates were incubated for another 5 hr. in the incubator and cells were harvested by filtration on a glass fiber filter using a Tomtec Harvester 96. Incorporated thymidine was counted on a Wallac β plate scintillation counter.

Results

A. Effect of MTG concentration on KGF-2 activity

Figure 5:
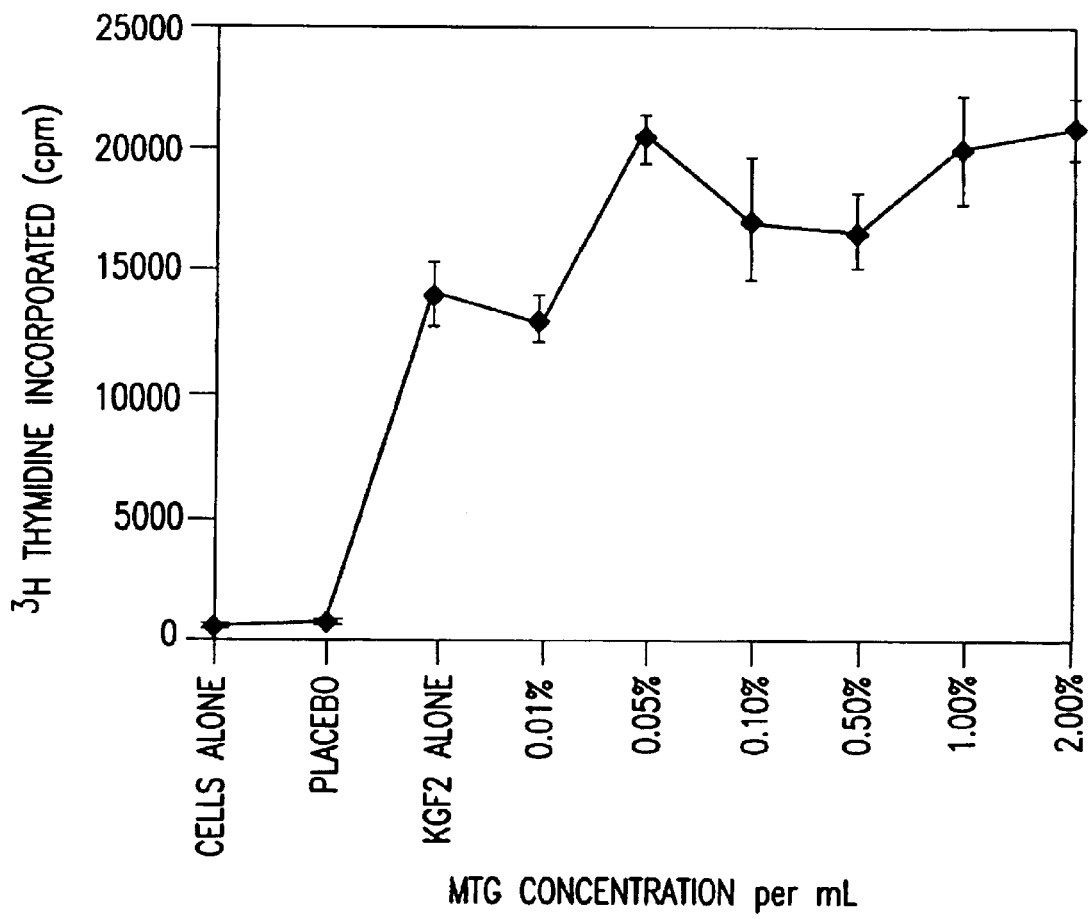
FIG. 5 shows the effect of monothiolglycerol on KGF-2 bioactivity.

The cell proliferation assay was carried out with KGF-2 exposed to different concentrations of monothioglycerol (MTG). Control samples contained no excipient. With MTG, stimulation of KGF-2 activity was observed with various concentrations of MTG is shown in FIG. 5. The increase in activity was between 10–150% of control depending on the concentration of MTG used. This enhancement of cell proliferation activity was not observed with other members of this growth factor family. From these observations, it was concluded that stimulation of KGF-2 activity by MTG was quite specific.

Conclusions

Monothioglycerol appears to specifically stimulate the in vitro cell proliferation activity of KGF-2.

Example 6

KGF-2 Gel Formulation with Citrate

The following ingredients were mixed to create a KGF-2 formulation is a liquid at room temperature and that subsequently gels upon application to skin.
   20 mM sodium citrate,
   125 mM sodium chloride,
   20 1 mM disodium EDTA,
   17% Pluronic 127, pH 6.0,
   water.

Example 7

KGF-2 Gel Formulation with Acetate

The following ingredients were mixed to create a KGF-2 formulation that can gel upon application to skin.
   20 mM sodium acetate,
   125 mM sodium chloride,
   1 mM disodium EDTA,
   17% Pluronic 127, pH 6.0,
   water.

Example 8

Liquid KGF-2 Formulations

The suitability of sodium citrate as a buffer in which to maintain KGF-2 Δ33 was evaluated in four separate formulations, and at three separate pHs: pH 5.0, pH 5.5 and pH 6.0.

Formulations:
   A. KGF-2 Δ33 1 or 2 mg/ml
      20 mM sodium citrate,
      125 mM sodium chloride,
      1 mM disodium EDTA,
      water.
   B. As in "A" above, further including 1% glycerol.
   C. As in "A" above, further including 0.05% methionine.
   D. As in "A" above, further including 1% monothioglycerol.

The concentration of KGF-2 Δ33 was 1 and 2 mg/ml in all of the above formulations.

2. Lyophilization Formulation

KGF-2 Δ33 was lyophilized in the presence of one of three bulking agents: mannitol, sucrose and trehalose.

Formulations
   A. 10 mM sodium citrate, 20 mM sodium chloride, 1 mM disodium EDTA and 4% mannitol, pH 6.0
   B. 10 mM sodium citrate, 20 mM sodium chloride, 1 mM disodium EDTA and 7% sucrose, pH 6.0
   C. 10 mM sodium citrate, 20 mM sodium chloride, 1 mM disodium EDTA and 8% trehalose, pH 6.0

The concentration of KGF-2 polypeptide was 3 mg/ml and 8 mg/ml. Evaluation parameters were RP-HPLC, SDS-PAGE, appearance, before and following reconstitution with water.

3. 10 mg/ml KGF-2 Lyophilization

Whether the formulation will permit lyophilization of the protein at 10 mg/ml was assessed as well as the protein's subsequent stability after reconstitution.

Formulation
   10 mM sodium citrate, 20 mM sodium chloride, 1 mM disodium EDTA and 4% mannitol, pH 6.0.

The lyophilized products were reconstituted with water or water containing 1% monothioglycerol.

Example 9

Thickening Agent Stability

The following formulations are prepared according to the methods of the previous examples. Configurations 1 and 2 are lyophilized KGF-2 alone; configurations 3 and 4 include the thickening agent as part of the lyo cake; and configurations 5–8 include the thickening agent as part of the liquid diluent.

| Config. # | Lyophilized vial | Liquid vial |
| --- | --- | --- |
| 1 | 7.0% sucrose, 10 mM sodium citrate, 20 mM NaCl, 1 mM EDTA, pH 6.2 0.05 mg/ml KGF-2 | water for injection |
| 2 | 7.0% sucrose, 10 mM sodium citrate, 20 mM NaCl, 1 mM EDTA, pH 6.2 1.0 mg/ml KGF-2 | water for injection |
| 3 | 0.46% HEC 7.0% sucrose, 10 mM sodium citrate, 20 mM NaCl, 1 mM EDTA, pH 6.2 0.05 mg/ml KGF-2 | water for injection |
| 4 | 0.46 HEC 7.0% sucrose, 10 mM sodium citrate, 20 mM NaCl, 1 mM EDTA, pH 6.2 1.0 mg/ml KGF-2 | water for injection |
| 5 | 7.0% sucrose, 10 mM sodium citrate, 20 mM NaCl, 1 mM EDTA, pH 6.2 0.05 mg/ml KGF-2 | 0.46% HEC 10 mM sodium citrate pH 6.2 |
| 6 | 7.0% sucrose, 10 mM sodium citrate, 20 mM NaCl, 1 mM EDTA, pH 6.2 1.0 mg/ml KGF-2 | 0.46% HEC 10 mM sodium citrate pH 6.2 |

-continued

| Config. # | Lyophilized vial | Liquid vial |
|---|---|---|
| 7 | 7.0% sucrose, 10 mM sodium citrate, 20 mM NaCl, 1 mM EDTA, pH 6.2 0.05 mg/ml KGF-2 | 0.92% HPMC 10 mM sodium citrate pH 6.2 |
| 8 | 7.0% sucrose, 10 mM sodium citrate, 20 mM NaCl, 1 mM EDTA, pH 6.2 1.0 mg/ml KGF-2 | 0.46% HPMC 10 mM sodium citrate pH 6.2 |

Example 10

The use of KGF-2 in treating chronic wounds is expected to involve multiple, topical applications of the drug. The lyophilized configuration requires a separate vial of drug product to be reconstituted per application due to the absence of any preservative. This results in a significant amount of drug waste, as well as a more labor-intensive product preparation to be performed at every dosing. Ideally, the commercial configuration of KGF-2 would involve a single vial of KGF-2 that could be used for multiple applications. To investigate the feasibility of this configuration, the compatibility of KGF-2 with preservatives was examined.

Preservatives were selected from a list of FDA approved compounds. The five candidate preservatives selected were based on prevalence in the Physicians Desk Reference (PDR) as well as previous published work with biopharmaceuticals. Since the formulation and dosage form have not been finalized, strong emphasis was not initially placed on compatibility with the elastomeric closure or stability at pH 6.2. Concentrations were selected based on literature values as well as FDA/USP and BP guidelines. The table below presents the five candidate preservatives examined in this study.

| Preservative | Concentration | Comments |
|---|---|---|
| Benzyl Alcohol | 0.9% | 1. Should not be used in newborns 2. Optimum activity at pH < 5 |
| Chlorobutanol | 0.5% | 1. Incompatible with rubber closures 2. Poor stability at neutral pH |
| Phenol | 0.5% | 1. Should not be lyophilized 2. May be caustic when used topically 3. Good effectiveness under acidic conditions |
| Cresol | 0.3% | 1. Should not be lyophilized 2. May be caustic when used topically 3. Good effectiveness at pH 4–8 |
| Parabens[1] | 0.2% | 1. Good effectiveness at pH 4–8 2. May be irritant for injection |

[1]"Parabens" is defined in this example as 0.18% methylparaben and 0.02% propylparaben.

In order to utilize a preservative, two criteria must be met. First, compatibility and stability with the drug product must be established. Second, the microbial effectiveness must be established (per USP <51>). The purpose of this study was to examine short-term compatibility of KGF-2 with these preservatives.

MATERIALS AND METHODS

Formulations

All chemicals were purchased from Spectrum and were USP/NF grade or equivalent. KGF-2 was diafiltered into a base formulation buffer containing one of the following: 0.9% benzyl alcohol, 0.5% chlorobutanol, 0.5% phenol, 0.3% m-cresol, or 0.18% methyl paraben+0.02% propel paraben ("parabens"). Diafiltration was performed in an Amicon stirred-cell with a Biomax 10 kD membrane. All processing was carried out at 2–8° C. A total of 5 buffer exchanges were performed for each diafiltration. Recoveries during diafiltration were >90%. KGF-2 was diluted to 1.0 mg/mL and filled (1.0 mL) into 2 mL Schott Purform vials, and sealed with a Diakyo D-7771 serum stopper and aluminum crimp seal. Vials were stored at −80° C., 2–8° C., and 250° C./60% relative humidity. Formulations that contained precipitation were 0.2 μm filtered prior to further analysis.

Appearance

Visual inspection was performed using forward illuminating fluorescent light against a black and white background under normal magnification.

SDS-PAGE

SDS-PAGE was performed under non-reducing conditions using a 16% Tris-glycine Novex gel. A total of 2 μg of KGF-2 was loaded per lane. The gels were run under constant voltage (125 V) for approximately 2 hours. Staining was performed using a Daiichi silver stain kit according to the manufacturer's instructions.

Bioactivity

Bioactivity of KGF-2 is determined using a murine lymphocyte cell line, Baf3 2b, that has been stably transected with the fibroblast growth factor 2iiib receptor. Activity is based on cellular proliferation as measured by the incorporation of [methyl-$^3$H] thymidine after exposure to KGF-2.

Differential Scanning Calorimetry (DSC)

DSC thermograms of each formulation were obtained on a Calorimetry Sciences Nano DSC (model 5100). Scans were performed from 5° C. to 80° C. at a rate of 1° C./minute in both the heating and cooling direction. The melting temperature ($T_m$) was measured as the apex of the thermal transition. No signal was observed in the cooling direction in any of the samples, indicating that the unfolding was irreversible.

RP-HPLC (Concentration, Purity, Percent Oxidized)

RP-HPLC was performed on a Waters 2690 Alliance system equipped with a Waters 996 photodiode array detector. A Waters Delta-Pak C 18 column (2.1×150 mm, 5 μm, 300 Å) was used for separation using a linear gradient of solvent A (0.1% TFA in water) to solvent B (0.07% TFA in acetonitrile). Concentration was determined by correlating the total peak area of an unknown to a standard curve using an internal reference standard of known concentration. A typical chromatogram of the standard is shown below. Two major peaks are separated and have been identified previously as the intact KGF-2 peak and an oxidized form of KGF-2. Percent oxidized is reported as an area percentage of the total area. Percent purity is the area percent attributed to the sum of the intact and oxidized form.

Results

Chlorobutanol and parabens show promising compatibility with KGF-2 at 2–8° C. Benzyl alcohol, m-cresol, and phenol cause rapid aggregation of KGF-2 when stored at 2–8° C. When stored at 25° C., all formulations have poor appearance after one week of storage. KGF-2 precipitates out of solution when subjected to freeze/thaw conditions in the presence of m-cresol and phenol.

All preservatives tested have a slight destabilizing effect on KGF-2's thermal stability. The melting temperature, as determined by DSC, shows an approximate 5° C. drop in the presence of all of the preservatives. Of the preservatives tested, the parabens have the least impact.

The specific activity of KGF-2 is not affected by the presence of any of the preservatives tested. Although the total activity of the formulations stored at 25° C. does decrease after six weeks storage due to precipitation of KGF-2, the soluble protein in the chlorobutanol, parabens, and benzyl alcohol formulations retained its specific activity.

At 2–8° C. storage, all formulations remain within 10% of their starting concentrations as determined by RP-HPLC. When stored at 25° C., the formulations containing m-cresol or phenol exhibited the fastest rate of precipitation. Of the formulations tested, those containing parabens or chlorobutanol retain the most KGF-2 in solution during the course of the short-term stability.

Benzyl alcohol causes rapid oxidation of KGF-2, followed by continued degradation of the oxidized form. This is exhibited by a high initial level of oxidation (formed during diafiltration), followed by a slow transition into further oxidized forms. When stored at 2–8° C., the remaining formulations have comparable oxidation rates of approximately 4% per month. When stored at 25° C., the oxidation rates increase to 30–40% per month. Of the formulations tested, the one containing parabens has the slowest average oxidation rate.

Purity is determined as the sum of the main and oxidized form of KGF-2 as a percentage of the total chromatographic area. The formulations containing benzyl alcohol or phenol exhibit an initially low purity, followed by a rise and then gradual loss of purity. This corresponds with a sharp increase at time zero of a chromatographic peak that appears to correspond with soluble aggregate. As precipitate continues to form, this peak disappears with no subsequent increase in any other peak area. When stored at 25° C., the formulation containing parabens retains the highest purity.

SDS-PAGE shows a slight increase in dimer band in the benzyl alcohol containing formulation at time zero as well as six weeks storage. Slight lane streaking and increased levels of dimer are observed in the formulations stored at 25° C.

Conclusions

KGF-2 is incompatible with benzyl alcohol, m-cresol, and phenol under the conditions examined. In these formulations, aggregation followed by precipitation was the primary pathway for degradation. Of the preservatives tested, methyl/propyl paraben has the least impact on the short-term stability of KGF-2.

Example 11

KGF-2 in a Lyophilized Formulation

The following ingredients were mixed to create a KGF-2 Δ33 premix formulation.

3.3 mg/ml KGF-2 Δ33, 10 mM sodium citrate, 20 mM sodium chloride, 1 mM EDTA,

2% w/v glycine 0.5% w/v sucrose, water (removed upon lyophilization)

pH 6.2.

The formulation was subsequently lyophilized according to the second lyophilzation cycle described above.

This formulation retained its in vitro bioactivity for up to 12 months at storage conditions at or below 25° C.

Example 12

KGF-2 Topical Formulation

The following ingredients were mixed to create a KGF-2 formulation for topical application.

1.0 mg/ml KGF-2 Δ33, 0.46% hydroxyethylcellulose (HEC)

7% sucrose 20 mM sodium citrate, 20 mM sodium chloride, 1 mM EDTA pH 6.2.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A pharmaceutical composition, comprising:
   (a) a polypeptide comprising Ser (69)–Ser (208) of SEQ ID NO:2 in a concentration range of about 0.02 to about 40 mg/ml (w/v);
   (b) a buffer having a buffering capacity of between about 5.0 and about 8.0 at a concentration range of about 5 mM to about 50 mM;
   (c) a pharmaceutically acceptable diluent to bring the composition to a designated volume; and
   (d) a preservative consisting of a mixture of methyl paraben and propyl paraben, wherein said methyl paraben is at a concentration of 0.1% to 0.2% and said propyl paraben is at a concentration of 0.01% to 0.05%, wherein said polypeptide has KGF-2 activity.

2. The pharmaceutical composition of claim 1, further comprising:
   (a) a chelating agent at a concentration range of about 1 mM to about 10 mM; and
   (b) a tonicifier at a concentration range of about 0 mM to about 150 mM.

3. The pharmaceutical composition of claim 1, further comprising one of:
   (a) about 0.5% to about 2% w/v glycerol,
   (b) about 0.1% to about 1% w/v methionine, or
   (c) about 0.1% to about 2% w/v monothioglycerol.

4. The pharmaceutical composition of claim 1, wherein said polypeptide is present in a concentration range of about 0.05 to about 30 mg/ml (w/v).

5. The pharmaceutical composition of claim 1, wherein said diluent is water.

6. The pharmaceutical composition of claim 1, wherein said pH is from about pH 5.5 to about pH 6.5.

7. The pharmaceutical composition of claim 1, wherein said buffer is selected from the group consisting of phosphonic, acetic, aconitic, citric, glutaric, malic, succinic carbonic acid, and an alkali or alkaline earth salt thereof.

8. The pharmaceutical composition of claim 1, wherein said buffer is present in a concentration range of about 5 mM to about 30 mM.

9. The pharmaceutical composition of claim 1, further comprising a stabilizing amount of one or more of (a) an antioxidant or (b) a thiol-compound.

10. The pharmaceutical composition of claim 1, wherein said composition is maintained at a temperature at or below −20° C.

11. The pharmaceutical composition of claim 1, wherein said polypeptide is selected from the group consisting of (i) Ser (69)–Ser (208) of SEQ ID NO:2; (ii) Ser (69)–Ser (208) of SEQ ID NO:2 with a methionine at the N-terminus; and (iii) a mixture of (i) and (ii).

12. The pharmaceutical composition of claim 1, further comprising a bulking agent.

13. The pharmaceutical composition of claim 1, further comprising a thickening agent in an amount effective to raise the viscosity to about 50 to about 10,000 cps.

14. The pharmaceutical composition of claim 1, further comprising a thickening agent present in a concentration of 0 to 5% (w/w).

15. The pharmaceutical composition of claim 1, further comprising a thickening agent, wherein said thickening agent is a water soluble etherified cellulose derivative selected from the group consisting of methyl cellulose, hydroethyl cellulose, hydroxy propyl cellulose, hydroxy propyl methylcellulose, or carboxymethyl cellulose, wherein said etherified cellulose derivative has a molecular weight of about 50,000 to about 700,000 and is present in a concentration of about 0 to about 20% by weight.

16. The composition of claim 1, further comprising a gelling agent in an amount effective to raise the viscosity to about 0 to about 10,000 cps at room temperature.

17. The pharmaceutical composition of claim 1, wherein said polypeptide is present in a concentration range of about 0.01 mg/ml to about 10 mg/ml (w/v).

18. The pharmaceutical composition of claim 1, further comprising one of:
   (a) lysine;
   (b) hydroxypropyl-β-cyclodextrin; and
   (c) sulfated-β-cyclodextrin;
or combinations thereof.

19. The pharmaceutical composition of claim 1, wherein said mixture consists of 0.18% methyl paraben and 0.02% propyl paraben.

20. The pharmaceutical composition of claim 2, wherein said tonicifier is selected from the group consisting of NaCl, glycine, sucrose, mannitol, and mixtures thereof.

21. The pharmaceutical composition of claim 2, wherein said chelating agent is EDTA at a concentration of about 1 mM, and said tonicifier is present at a concentration of about 125 mM.

22. The pharmaceutical composition of claim 2, further comprising a bulking agent.

23. The pharmaceutical composition of claim 4, wherein said polypeptide is present in a concentration range of about 0.1 to about 20 mg/ml (w/v).

24. The pharmaceutical composition of claim 23, wherein said polypeptide is present in a concentration range of about 0.2 to 4 mg/ml (w/v).

25. The pharmaceutical composition of claim 6, wherein said pH is about pH 6.2.

26. The pharmaceutical composition of claim 7, wherein said buffer is a phosphate, acetate or citrate salt.

27. The pharmaceutical composition of claim 7, wherein said buffer is a citrate salt.

28. The pharmaceutical composition of claim 8, wherein said buffer is a citrate salt present in a concentration of from about 10 mM to about 20 mM.

29. The pharmaceutical composition of claim 12, wherein said bulking agent is selected from the group consisting of sucrose, glycine, mannitol, trehalose, and mixtures thereof.

30. The pharmaceutical composition of claim 12, wherein said pH is about pH 6.2.

31. The pharmaceutical composition of claim 12, wherein said diluent is water.

32. The pharmaceutical composition of claim 12, wherein said buffer is selected from the group consisting of phosphonic, acetic, aconitic, citric, glutaric, malic, succinic carbonic acid, and an alkali or alkaline earth salt thereof.

33. The pharmaceutical composition of claim 12, wherein said buffer is added in a concentration from about 5 mM to about 50 mM.

34. The pharmaceutical composition of claim 12, further including a stabilizing amount of one or more of (a) an antioxidant, or (b) a thiol-compound.

35. The pharmaceutical composition of claim 12, further comprising a thickening agent in an amount effective to raise the viscosity to about 50 to about 10,000 cps.

36. The composition of claim 21, further comprising a gelling agent in an amount effective to raise the viscosity to about 0 to about 10,000 cps at room temperature.

37. The pharmaceutical composition of claim 29, wherein said bulking agent is sucrose or a mixture of sucrose and glycine.

38. The pharmaceutical composition of claim 29, wherein said bulking agent is present in a concentration of about 2% to about 10% w/v.

39. The pharmaceutical composition of claim 29, wherein said bulking agent is 5% mannitol, 7% sucrose, 8% trehalose, or 2% glycine +0.5% sucrose.

40. The pharmaceutical composition of claim 31, wherein over 90% of the water is removed by lyophilization.

41. The pharmaceutical composition of claim 32, wherein said buffer is a phosphate or citrate salt.

42. The pharmaceutical composition of claim 33, wherein said buffer is citrate at a concentration of about 10 mM.

43. The pharmaceutical composition of claim 40, which is reconstituted in with an amount of sterile water effective to maintain isotonic conditions of 290 mOsm.

44. The pharmaceutical composition of claim 40, wherein said composition is reconstituted in sterile water containing a stabilizing amount of an antioxidant comprising: a) about 0.01% to about 2% w/v monothioglycerol, b) about 0.01% to about 2% w/v ascorbic acid, c) about 0.01% to about 2% w/v methionine or d) combinations thereof.

45. The pharmaceutical composition of claim 41, wherein said buffer is a citrate salt.

46. The pharmaceutical composition of claim 13, wherein said thickening agent is present in an amount effective to raise the viscosity to about 50 to about 1,000 cps.

47. The pharmaceutical composition of claim 13, wherein said thickening agent is a water soluble etherified cellulose or a carbomer.

48. The pharmaceutical composition of claim 46, wherein said thickening agent in an amount effective to raise the viscosity to about 200 to about 300 cps.

49. The pharmaceutical composition of claim 47, wherein said etherified cellulose is an alkyl cellulose, hydroxyalkyl cellulose, carboxyalkyl cellulose or alkylhydroxyalkyl cellulose.

50. The pharmaceutical composition of claim 47, wherein said etherified cellulose is methylcellulose, hydroxyethyl cellulose, hydroxy propyl cellulose, hydroxy propyl methylcellulose, or carboxymethyl cellulose.

51. The pharmaceutical composition of claim 48, wherein said buffer is citrate in a concentration of about 10 mM to about 50 mM.

52. The pharmaceutical composition of claim 51, wherein said buffer is citrate in a concentration of about 10 mM to about 20 mM citrate.

53. The pharmaceutical composition of claim 51, wherein said bulking agent is sucrose in a concentration of about 0% to about 5% sucrose.

54. The pharmaceutical composition of claim 53, wherein said thickening agent is added directly to a liquid formulation and thereafter lyophilized.

55. The pharmaceutical composition of claim 53, wherein said thickening agent is added to a lyophilized formulation by reconstituting said formulation by adding a suitable diluent having a thickening agent dissolved therein.

56. The pharmaceutical composition of claim 15, wherein said etherified cellulose derivative has a molecular weight of about 80, 000 to about 240,000 and is present in a concentration of about 2% to about 8% by weight.

57. The composition of claim 16, wherein said gel forming agent is a water-soluble polymer capable of forming a viscous aqueous solution, or non-water soluble, water-swellable polymer capable of forming a viscous solution.

58. The composition of claim 57, wherein said gel forming agent is a high molecular weight polymer selected from the group consisting of vinyl polymer, polyoxyethylene-polyoxypropylene copolymer, polysaccharide, protein, poly (ethylene oxide), acrylamide polymer or a salt thereof.

59. The composition of claim 58, wherein said gel forming agent is (1) a vinyl polymer selected from the group consisting of polyacrylic acid, polymethacrylic acid, polyvinyl pyrrolidone polyvinyl alcohol, and salts and esters thereof; or (2) a polysaccharide selected from the group consisting of a cellulose derivative, a glycosaminoglycan, agar, pectin, alginic acid, dextran, α-amylose, amylopectin, chitosan, or salts esters thereof.

60. The composition of claim 58, wherein said gel forming agent is a glycosaminoglycan selected from the group consisting of hyaluronic acid, chondroitin, chondroitin-4-sulfate, heparan sulfate, heparin and salts and esters thereof.

61. The composition of claim 60, wherein said glycosaminoglycan is present in combination with collagen, gelatin, or fibronectin.

62. The composition of claim 58, wherein said gel forming agent is an acrylamide polymer selected from the group consisting of a polyacrylamide or a polymethacrylamide.

63. The composition of claim 58, wherein said gel forming agent is a polyoxyethylene-polyoxypropylene block copolymer.

64. The composition of claim 63, which comprises about 10 to about 60% by weight of a polyoxyethylene-polyoxypropylene block copolymer having an average molecular weight of about 500 to 50,000.

65. The composition of claim 64, which comprises about 14 to about 18% by weight of a polyoxyethylene-polyoxypropylene block copolymer having a molecular weight in the range 1,000 to 15,000.

66. A pharmaceutical composition comprising:
(a) about 1.0 mg/ml of a polypeptide comprising Ser (69)–Ser (208) of SEQ ID NO:2;
(b) 20 mM citrate, pH 5–5.5; and
(c) 0.01% polysorbate 80.

67. The pharmaceutical composition of claim 66, further comprising 1 mM EDTA.

68. The pharmaceutical composition of claim 66, wherein said polypeptide is selected from the group consisting of: (i) Ser (69)–Ser (208) of SEQ ID NO:2; (ii) Ser (69)–Ser (208) of SEQ ID NO:2 with a methionine at the N-terminus; and (iii) a mixture of (i) and (ii).

69. A pharmaceutical composition comprising:
(a) about 3.3 mg/ml of a polypeptide comprising Ser (69)–Ser (208) of SEQ ID NO:2;
(b) 10 mM sodium citrate;
(c) 20 mM sodium chloride;
(d) 1 mM EDTA
(e) 2% w/v glycine;
(f) 0.5% w/v sucrose; and
(g) water;
wherein the composition is at a pH or about 6.2.

70. The pharmaceutical composition of claim 69, wherein over 90% of the water is removed by lyophilization.

71. The pharmaceutical composition of claim 69, wherein said polypeptide is selected from the group consisting of: (i) Ser (69)–Ser (208) of SEQ ID NO:2; (ii) Ser (69)–Ser (208) of SEQ ID NO:2 with a methionine at the N-terminus; and (iii) a mixture of (i) and (ii).

72. A pharmaceutical composition comprising:
(a) about 1.0 mg/ml of a polypeptide comprising Ser (69)–Ser (208) of SEQ ID NO:2;
(b) 0.46% hydroxyethylcellulose;
(c) 7% sucrose;
(d) 20 mM sodium citrate;
(e) 20 mM sodium chloride;
(f) 1 mM EDTA;
wherein the composition is at a pH of about 6.2.

73. The pharmaceutical composition of claim 72, wherein said polypeptide is selected from the group consisting of: (i) Ser (69)–Ser (208) of SEQ ID NO:2; (ii) Ser (69)–Ser (208) of SEQ ID NO:2 with a methionine at the N-terminus; and (iii) a mixture of (i) and (ii).

74. A pharmaceutical composition produced by the process of admixing:
(a) a polypeptide comprising Ser (69)–Ser (208) of SEQ ID NO:2 in a concentration range of about 0.02 to about 40 mg/ml (w/v);
(b) a buffer having a buffering capacity of about pH 5.0 to about pH 8.0 at a concentration range of about 5 mM to about 50 mM;
(c) a pharmaceutically acceptable diluent to bring the composition to a designated volume; and
(d) a preservative consisting of a mixture of methyl paraben and propyl paraben, wherein said methyl paraben is at a concentration of 0.1% to 0.2% and said propyl paraben is at a concentration of 0.01% to 0.05%, wherein said polypeptide has KGF-2 activity.

75. The pharmaceutical composition of claim 74, further comprising one or more of:
(a) a chelating agent at a concentration no greater than about 10 mM; and
(b) a tonicifier at a concentration no greater than about 150 mM.

76. The pharmaceutical composition of claim 74, further comprising one of:
(a) about 0.5% to about 2% w/v glycerol,
(b) about 0.1% to about 1% w/v methionine; and
(c) about 0.1% to about 2% w/v monothioglycerol.

77. The pharmaceutical composition of claim 74, wherein said polypeptide is present in a concentration range of about 0.05 to about 30 mg/ml (w/v).

78. The pharmaceutical composition of claim 74, wherein said diluent is water.

79. The pharmaceutical composition of claim 74, wherein said pH is from about pH 5.5 to about 6.5.

80. The pharmaceutical composition of claim 74, wherein said buffer is selected from the group consisting of phosphonic, acetic, aconitic, citric, glutaric, malic, succinic carbonic acid, and an alkali or alkaline earth salt thereof.

81. The pharmaceutical composition of claim 74, wherein said buffer is present in a concentration range of about 5 mM to about 30 mM.

82. The pharmaceutical composition of claim 74, further comprising a stabilizing amount of one or more of (a) an antioxidant or (b) a thiol-compound.

83. The pharmaceutical composition of claim 74, wherein said polypeptide is selected from the group consisting of: (i) Ser (69)–Ser (208) of SEQ ID NO:2; (ii) Ser (69)–Ser (208) of SEQ ID NO:2 with a methionine at the N-terminus; and (iii) a mixture of (i) and (ii).

84. The pharmaceutical composition of claim 74, further comprising a bulking agent.

85. The pharmaceutical composition of claim 74, further comprising a thickening agent in an amount effective to raise the viscosity to about 50 to about 10,000 cps.

86. The pharmaceutical composition of claim 74, further comprising a thickening agent present in a concentration of 0 to 5% (w/w).

87. The pharmaceutical composition of claim 74, further comprising a thickening agent, wherein said thickening agent is a water soluble etherified cellulose derivative selected from the group consisting of methyl cellulose, hydroethyl cellulose, hydroxy propyl cellulose, hydroxy propyl methycellulose, or carboxymethyl cellulose, wherein said etherified cellulose derivative has a molecular weight of about 50,000 to about 700,000 and is present in a concentration of about 0 to about 20% by weight.

88. The composition of claim 74, further comprising a gelling agent in an amount effective to raise the viscosity to about 0 to about 10,000 cps at room temperature.

89. The pharmaceutical composition of claim 74, wherein said polypeptide is present in a concentration range of about 0.01 mg/ml to about 10 mg/ml (w/v).

90. The pharmaceutical composition of claim 74, further comprising one of:
(a) lysine;
(b) hydroxypropyl-β-cyclodextrin; and
(c) sulfated-β-cyclodextrin;
or combinations thereof.

91. The pharmaceutical composition of claim 74, wherein said mixture consists of 0.18% methyl paraben and 0.02% propyl paraben.

92. The pharmaceutical composition do claim 75, wherein said tonicifier is selected from the group consisting of NaCl, glycine, sucrose, mannitol, and mixtures thereof.

93. The pharmaceutical composition of claim 75, wherein said chelating agent is EDTA at a concentration of about 1 mM, and said tonicifier is present at a concentration of about 125 mM.

94. The pharmaceutical composition of claim 75, further comprising a bulking agent.

95. The pharmaceutical composition of claim 77, wherein said polypeptide is present in a concentration range of about 0.1 to about 20 mg/ml (w/v).

96. The pharmaceutical composition of claim 79, wherein said pH is about pH 6.0.

97. The pharmaceutical composition of claim 80, wherein said buffer is a phosphate, acetate or citrate salt.

98. The pharmaceutical composition of claim 80, wherein said buffer is a citrate salt.

99. The pharmaceutical composition of claim 81, wherein said buffer is a citrate salt present in a concentration of from about 10 mM to about 20 mM.

100. The pharmaceutical composition of claim 74, wherein said composition is maintained at a temperature at or below −20° C.

101. The pharmaceutical composition of claim 95, wherein said polypeptide is present in a concentration range of about 0.2 to 4 mg/ml (w/v).

102. The pharmaceutical composition of claim 84, wherein said bulking agent is selected from the group consisting of sucrose, glycine, mannitol, trehalose, and mixtures thereof.

103. The pharmaceutical composition of claim 102, wherein said bulking agent is sucrose or a mixture of sucrose and glycine.

104. The pharmaceutical composition of claim 102, wherein said bulking agent is present in a concentration of about 2% to about 10% w/v.

105. The pharmaceutical composition of claim 102, wherein said bulking agent is 5% mannitol, 7% sucrose, 8% trehalose, or 2% +0.5% sucrose.

106. The pharmaceutical composition of claim 84, wherein said pH is about pH 6.2.

107. The pharmaceutical composition of claim 84, wherein said diluent is water.

108. The pharmaceutical composition of claim 107, wherein over 90% of the water is removed by lyophilization.

109. The pharmaceutical composition of claim 108, which is reconstituted in with an amount of sterile water effective to maintain isotonic conditions of 290 mOsm.

110. The pharmaceutical composition of claim 108, wherein said composition is reconstituted in sterile water containing a stabilizing amount of an antioxidant comprising: a) about 0.01% to about 2% w/v monothioglycerol, b) about 0.01% to about 2% w/v ascorbic acid, c) about 0.01% to about 2% w/v methionine or d) combinations thereof.

111. The composition of claim 84, further comprising a gelling agent in an amount effective to raise the viscosity to about 0 to about 10,000 cps at room temperature.

112. The pharmaceutical composition of claim 84, wherein said buffer is selected from the group consisting of phosphonic, acetic, aconitic, citric, glutaric, malic, succinic carbonic acid, and an alkali or alkaline earth salt thereof.

113. The pharmaceutical composition of claim 112, wherein said buffer is a phosphate or citrate salt.

114. The pharmaceutical composition of claim 113, wherein said buffer is a citrate salt.

115. The pharmaceutical composition of claim 84, wherein said buffer is added in a concentration from about 5 mM to about 50 mM.

116. The pharmaceutical composition of claim 115, wherein said buffer is citrate at a concentration of about 10 mM.

117. The pharmaceutical composition of claim 84, further including a stabilizing amount of one or more of (a) an antioxidant, or (b) a thiol-compound.

118. The pharmaceutical composition of claim 84, further comprising a thickening agent in an amount effective to raise the viscosity to about 50 to about 10,000 cps.

119. The pharmaceutical composition of claim 85, wherein said thickening agent is present in an amount effective to raise the viscosity to about 50 to about 10,000 cps.

120. The pharmaceutical composition of claim 119, wherein said thickening agent in an amount effective to raise the viscosity to about 200 to about 300 cps.

121. The pharmaceutical composition of claim 120, wherein said buffer is citrate in a concentration of about 10 mM to about 50 mM.

122. The pharmaceutical composition of claim 121, wherein said buffer is citrate in a concentration of about 10 mM to about 20 mM citrate.

123. The pharmaceutical composition of claim 121, wherein said bulking agent is sucrose in a concentration of about 0% to about 5% sucrose.

124. The pharmaceutical composition of claim 123, wherein said thickening agent is added directly to a liquid formulation and thereafter lyophilized.

125. The pharmaceutical composition of claim 123, wherein said thickening agent is added to a lyophilized formulation by reconstituting said formulation by adding a suitable diluent having a thickening agent dissolved therein.

126. The pharmaceutical composition of claim 85, wherein said thickening agent is a water soluble etherified cellulose or a carbomer.

127. The pharmaceutical composition of claim 126, wherein said etherified cellulose is an alkyl cellulose, hydroxyalkyl cellulose, carboxyalkyl cellulose or alkylhydroxyalkyl cellulose.

128. The pharmaceutical composition of claim 126, wherein said etherified cellulose is methylcellulose, hydroxyethyl cellulose, hydroxy propyl cellulose, hydroxy propyl methylcellulose, or carboxymethyl cellulose.

129. The pharmaceutical composition of claim 87, wherein said etherified cellulose derivative has a molecular weight of about 80,000 to about 240,000 and is present in a concentration of about 2% to about 8% by weight.

130. The composition of claim 88, wherein said gel forming agent is a water-soluble polymer capable of forming a viscous aqueous solution, or non-water soluble, water-swellable polymer capable of forming a viscous solution.

131. The composition of claim 130, wherein said gel forming agent is a high molecular weight polymer selected from the group consisting of vinyl polymer, polyoxyethylene-polyoxypropylene copolymer, polysaccharide, protein, poly(ethylene oxide), acrylamide polymer or a salt thereof.

132. The composition of claim 131, wherein said gel forming agent is (1) a vinyl polymer selected from the group consisting of polyacrylic acid, polymethacrylic acid, polyvinyl pyrrolidone polyvinyl alcohol, and salts and esters thereof; or (2) a polysaccharide selected from the group consisting of a cellulose derivative, a glycosaminoglycan, agar, pectin, alginic acid, dextran, α-amylose, amylopectin, chitosan, or salts esters thereof.

133. The composition of claim 131, wherein said gel forming agent is a glycosaminoglycan selected from the group consisting of hyaluronic acid, chondroitin, chondroitin-4-sulfate, heparan sulfate, heparin and salts and esters thereof.

134. The composition of claim 133, wherein said glycosaminoglycan is present in combination with collagen, gelatin, or fibronectin.

135. The composition of claim 131, wherein said gel forming agent is an acrylamide polymer selected from the group consisting of a polyacrylamide or a polymethacrylamide.

136. The composition of claim 131, wherein said gel forming agent is a polyoxyethylene-polyoxypropylene block copolymer.

137. The composition of claim 136, which comprises about 10 to about 60% by weight of a polyoxyethylene-polyoxypropylene block copolymer having an average molecular weight of about 500 to 50,000.

138. The composition of claim 137, which comprises about 14 to about 18% by weight of a polyoxyethylene-polyoxypropylene block copolymer having a molecular weight in the range 1,000 to 15,000.

139. A pharmaceutical composition produced by the process of admixing:
   (a) about 1.0 mg/ml of a polypeptide comprising Ser (69)–Ser (208) of SEQ ID NO:2;
   (b) 20 mM citrate, pH 5–5.5; and
   (c) 0.01% polysorbate 80.

140. The pharmaceutical composition of claim 139, further comprising 1 mM EDTA.

141. The pharmaceutical composition of claim 139, wherein said polypeptide is selected from the group consisting of: (i) Ser (69)–Ser (208) of SEQ ID NO:2; (ii) Ser (69)–Ser (208) of SEQ ID NO:2 with a methionine at the N-terminus; and (iii) a mixture of (i) and (ii).

142. A pharmaceutical composition produced by the process of admixing:
   (a) about 3.3 mg/ml of a polypeptide comprising Ser (69)–Ser (208) of SEQ ID NO:2;
   (b) 10 mM sodium citrate;
   (c) 20 mM sodium chloride;
   (d) 1 mM EDTA
   (e) 2% w/v glycine;
   (f) 0.5% w/v sucrose; and
   (g) water;
wherein the composition is at a pH or about 6.2.

143. The pharmaceutical composition of claim 142, wherein over 90% of the water is removed by lyophilization.

144. The pharmaceutical composition of claim 142, wherein said polypeptide is selected from the group consisting of: (i) Ser (69)–Ser (208) of SEQ ID NO:2; (ii) Ser (69)–Ser (208) of SEQ ID NO:2 with a methionine at the N-terminus; and (iii) a mixture of (i) and (ii).

145. A pharmaceutical composition produced by the process of admixing:
   (a) about 1.0 mg/ml of a polypeptide comprising Ser (69)–Ser (208) of SEQ ID NO:2;
   (b) 0.46% hydroxyethylcellulose;
   (c) 7% sucrose;
   (d) 20 mM sodium citrate;
   (e) 20 mM sodium chloride; and
   (f) 1 mM EDTA;
wherein the composition is at a pH of about 6.2.

146. The pharmaceutical composition of claim 145, wherein said polypeptide is selected from the group consisting of: (i) Ser (69)–Ser (208) of SEQ ID NO:2; (ii) Ser (69)–Ser (208) of SEQ ID NO:2 with a methionine at the N-terminus; and (iii) a mixture of (i) and (ii).

* * * * *

UNITED STATES PATENT AND TRADEMARK OFFICE
CERTIFICATE OF CORRECTION

PATENT NO. : 6,869,927 B1  
DATED : March 22, 2005  
INVENTOR(S) : Gentz et al.

It is certified that error appears in the above-identified patent and that said Letters Patent is hereby corrected as shown below:

Title page,  
Item [56], References Cited, FOREIGN PATENT DOCUMENTS, insert  
-- EP 0 619 115      10/1994  
   EP 0 518 697      12/1992 --;  
replace "8/1900" with -- 8/1990 --  
OTHER PUBLICATIONS, add -- European Search Report, Application No. EP 00 94 1186, dated December 19, 2002. --

Column 54,  
Line 43, replace "about 0.01 mg/ml" with -- about 0.1 mg/ml --

Signed and Sealed this

Ninth Day of August, 2005

JON W. DUDAS  
*Director of the United States Patent and Trademark Office*

SEQUENCE LISTING

```
<160> NUMBER OF SEQ ID NOS:  33

<210> SEQ ID NO 1
<211> LENGTH: 627
<212> TYPE: DNA
<213> ORGANISM: Homo sapiens
<220> FEATURE:
<221> NAME/KEY: CDS
<222> LOCATION: (1)..(624)

<400> SEQUENCE: 1 atg tgg aaa tgg ata ctg aca cat tgt gcc tca gcc ttt ccc cac ctg        48
Met Trp Lys Trp Ile Leu Thr His Cys Ala Ser Ala Phe Pro His Leu
  1               5                  10                  15 ccc ggc tgc tgc tgc tgc ttt ttg ttg ctg ttc ttg gtg tct tcc            96
Pro Gly Cys Cys Cys Cys Phe Leu Leu Leu Phe Leu Val Ser Ser
                 20                  25                  30 gtc cct gtc acc tgc caa gcc ctt ggt cag gac atg gtg tca cca gag       144
Val Pro Val Thr Cys Gln Ala Leu Gly Gln Asp Met Val Ser Pro Glu
```

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  |  | 45 |  |  |  |  |

```
gcc acc aac tct tct tcc tcc tcc ttc tcc tct cct tcc agc gcg gga      192
Ala Thr Asn Ser Ser Ser Ser Ser Phe Ser Ser Pro Ser Ser Ala Gly
     50                  55                  60 agg cat gtg cgg agc tac aat cac ctt caa gga gat gtc cgc tgg aga      240
Arg His Val Arg Ser Tyr Asn His Leu Gln Gly Asp Val Arg Trp Arg
 65                  70                  75                  80 aag cta ttc tct ttc acc aag tac ttt ctc aag att gag aag aac ggg      288
Lys Leu Phe Ser Phe Thr Lys Tyr Phe Leu Lys Ile Glu Lys Asn Gly
                 85                  90                  95 aag gtc agc ggg acc aag aag gag aac tgc ccg tac agc atc ctg gag      336
Lys Val Ser Gly Thr Lys Lys Glu Asn Cys Pro Tyr Ser Ile Leu Glu
            100                 105                 110 ata aca tca gta gaa atc gga gtt gtt gcc gtc aaa gcc att aac agc      384
Ile Thr Ser Val Glu Ile Gly Val Val Ala Val Lys Ala Ile Asn Ser
        115                 120                 125 aac tat tac tta gcc atg aac aag aag ggg aaa ctc tat ggc tca aaa      432
Asn Tyr Tyr Leu Ala Met Asn Lys Lys Gly Lys Leu Tyr Gly Ser Lys
    130                 135                 140 gaa ttt aac aat gac tgt aag ctg aag gag agg ata gag gaa aat gga      480
Glu Phe Asn Asn Asp Cys Lys Leu Lys Glu Arg Ile Glu Glu Asn Gly
145                 150                 155                 160 tac aat acc tat gca tca ttt aac tgg cag cat aat ggg agg caa atg      528
Tyr Asn Thr Tyr Ala Ser Phe Asn Trp Gln His Asn Gly Arg Gln Met
                165                 170                 175 tat gtg gca ttg aat gga aaa gga gct cca agg aga gga cag aaa aca      576
Tyr Val Ala Leu Asn Gly Lys Gly Ala Pro Arg Arg Gly Gln Lys Thr
            180                 185                 190 cga agg aaa aac acc tct gct cac ttt ctt cca atg gtg gta cac tca      624
Arg Arg Lys Asn Thr Ser Ala His Phe Leu Pro Met Val Val His Ser
        195                 200                 205 tag                                                                  627
```

<210> SEQ ID NO 2
<211> LENGTH: 208
<212> TYPE: PRT
<213> ORGANISM: Homo sapiens

<400> SEQUENCE: 2

```
Met Trp Lys Trp Ile Leu Thr His Cys Ala Ser Ala Phe Pro His Leu
 1               5                  10                  15

Pro Gly Cys Cys Cys Cys Cys Phe Leu Leu Leu Phe Leu Val Ser Ser
            20                  25                  30

Val Pro Val Thr Cys Gln Ala Leu Gly Gln Asp Met Val Ser Pro Glu
        35                  40                  45

Ala Thr Asn Ser Ser Ser Ser Ser Phe Ser Ser Pro Ser Ser Ala Gly
    50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140
```

```
Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Gly Gln Lys Thr
                180                 185                 190

Arg Arg Lys Asn Thr Ser Ala His Phe Leu Pro Met Val Val His Ser
        195                 200                 205
```

<210> SEQ ID NO 3
<211> LENGTH: 35
<212> TYPE: DNA
<213> ORGANISM: Homo sapiens

<400> SEQUENCE: 3
ggaccctcat gacctgccag gctctgggtc aggac          35

<210> SEQ ID NO 4
<211> LENGTH: 28
<212> TYPE: DNA
<213> ORGANISM: Homo sapiens

<400> SEQUENCE: 4
ggacagccat ggctggtcgt cacgttcg          28

<210> SEQ ID NO 5
<211> LENGTH: 29
<212> TYPE: DNA
<213> ORGANISM: Homo sapiens

<400> SEQUENCE: 5
ggacagccat ggttcgttgg cgtaaactg          29

<210> SEQ ID NO 6
<211> LENGTH: 31
<212> TYPE: DNA
<213> ORGANISM: Homo sapiens

<400> SEQUENCE: 6
ggacagccat ggaaaaaaac ggtaaagttt c          31

<210> SEQ ID NO 7
<211> LENGTH: 29
<212> TYPE: DNA
<213> ORGANISM: Homo sapiens

<400> SEQUENCE: 7 ggaccccat ggagaactgc ccgtagagc          29

<210> SEQ ID NO 8
<211> LENGTH: 32
<212> TYPE: DNA
<213> ORGANISM: Homo sapiens

<400> SEQUENCE: 8 ggaccccat ggtcaaagcc attaacagca ac          32

<210> SEQ ID NO 9
<211> LENGTH: 33
<212> TYPE: DNA
<213> ORGANISM: Homo sapiens

<400> SEQUENCE: 9

```
ggaccccat ggggaaactc tatggctcaa aag                                    33

<210> SEQ ID NO 10
<211> LENGTH: 37
<212> TYPE: DNA
<213> ORGANISM: Homo sapiens

<400> SEQUENCE: 10
ctgcccaagc ttattatgag tgtaccacca ttggaag                               37

<210> SEQ ID NO 11
<211> LENGTH: 36
<212> TYPE: DNA
<213> ORGANISM: Homo sapiens

<400> SEQUENCE: 11
ctgcccaagc ttattacttc agcttacagt cattgt                                36

<210> SEQ ID NO 12
<211> LENGTH: 32
<212> TYPE: DNA
<213> ORGANISM: Homo sapiens

<400> SEQUENCE: 12
gcggcacatg tcttacaacc acctgcaggg tg                                    32

<210> SEQ ID NO 13
<211> LENGTH: 28
<212> TYPE: DNA
<213> ORGANISM: Homo sapiens

<400> SEQUENCE: 13
gggcccaagc ttatgagtgt accaccat                                         28

<210> SEQ ID NO 14
<211> LENGTH: 36
<212> TYPE: DNA
<213> ORGANISM: Homo sapiens

<400> SEQUENCE: 14
ccggcggatc ccatatgtct tacaaccacc tgcagg                                36

<210> SEQ ID NO 15
<211> LENGTH: 35
<212> TYPE: DNA
<213> ORGANISM: Homo sapiens

<400> SEQUENCE: 15
ccggcggtac cttattatga gtgtaccacc attgg                                 35

<210> SEQ ID NO 16
<211> LENGTH: 426
<212> TYPE: DNA
<213> ORGANISM: Homo sapiens

<400> SEQUENCE: 16
atgtcttaca accacctgca gggtgacgtt cgttggcgta aactgttctc tttcaccaaa      60
tacttcctga aaatcgaaaa aaacggtaaa gtttctggga ccaagaagga gaactgcccg     120
tacagcatcc tggagataac atcagtagaa atcggagttg ttgccgtcaa agccattaac     180
agcaactatt acttagccat gaacaagaag gggaaactct atggctcaaa agaatttaac     240
```

-continued

```
aatgactgta agctgaagga gaggatagag gaaaatggat acaatacctg tgcatcattt    300
aactggcagc ataatgggag gcaaatgtat gtggcattga atggaaaagg agctccaagg    360
agaggacaga aaacacgaag gaaaacacc tctgctcact ttcttccaat ggtggtacac    420
tcataa                                                               426
```

<210> SEQ ID NO 17
<211> LENGTH: 141
<212> TYPE: PRT
<213> ORGANISM: Homo sapiens

<400> SEQUENCE: 17

```
Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Arg Lys
        115                 120                 125

Asn Thr Ser Ala His Phe Leu Pro Met Val Val His Ser
    130                 135                 140
```

<210> SEQ ID NO 18
<211> LENGTH: 20
<212> TYPE: DNA
<213> ORGANISM: Homo sapiens

<400> SEQUENCE: 18

```
caaccacctg cagggtgacg                                                20
```

<210> SEQ ID NO 19
<211> LENGTH: 78
<212> TYPE: DNA
<213> ORGANISM: Homo sapiens

<400> SEQUENCE: 19

```
aacggtcgac aaatgtatgt ggcactgaac ggtaaaggtg ctccacgtcg tggtcagaaa    60
acccgtcgta aaacacc                                                   78
```

<210> SEQ ID NO 20
<211> LENGTH: 76
<212> TYPE: DNA
<213> ORGANISM: Homo sapiens

<400> SEQUENCE: 20

```
gggcccaagc ttaagagtgt accaccattg gcagaaagtg agcagaggtg tttttacgac    60
gggttttctg accacg                                                    76
```

<210> SEQ ID NO 21

<211> LENGTH: 23
<212> TYPE: DNA
<213> ORGANISM: Homo sapiens

<400> SEQUENCE: 21
gccacataca tttgtcgacc gtt                                              23

<210> SEQ ID NO 22
<211> LENGTH: 19
<212> TYPE: DNA
<213> ORGANISM: Homo sapiens

<400> SEQUENCE: 22
gggcccaagc ttaagagtg                                                   19

<210> SEQ ID NO 23
<211> LENGTH: 23
<212> TYPE: DNA
<213> ORGANISM: Homo sapiens

<400> SEQUENCE: 23
gccacataca tttgtcgacc gtt                                              23

<210> SEQ ID NO 24
<211> LENGTH: 90
<212> TYPE: DNA
<213> ORGANISM: Homo sapiens

<400> SEQUENCE: 24
ctgcagggtg acgttcgttg gcgtaaactg ttctccttca ccaaatactt cctgaaaatc      60
gaaaaaaacg gtaaagtttc tggtaccaag                                       90

<210> SEQ ID NO 25
<211> LENGTH: 90
<212> TYPE: DNA
<213> ORGANISM: Homo sapiens

<400> SEQUENCE: 25
agctttaaca gcaacaacac cgatttcaac ggaggtgatt ccaggatgg agtacgggca       60 gttttctttc ttggtaccag aaactttacc                                       90

<210> SEQ ID NO 26
<211> LENGTH: 90
<212> TYPE: DNA
<213> ORGANISM: Homo sapiens

<400> SEQUENCE: 26
ggtgttgttg ctgttaaagc tatcaactcc aactactacc tggctatgaa caagaaaggt     60
aaactgtacg gttccaaaga atttaacaac                                       90

<210> SEQ ID NO 27
<211> LENGTH: 100
<212> TYPE: DNA
<213> ORGANISM: Homo sapiens

<400> SEQUENCE: 27
gtcgaccgtt gtgctgccag ttgaaggaag cgtaggtgtt gtaaccgttt tcttcgatac     60
gttctttcag tttacagtcg ttgttaaatt ctttggaacc                           100

<210> SEQ ID NO 28
<211> LENGTH: 25

-continued

<210> SEQ ID NO 28
<211> LENGTH: 25
<212> TYPE: DNA
<213> ORGANISM: Homo sapiens

<400> SEQUENCE: 28
gcggcgtcga ccgttgtgct gccag                                              25

<210> SEQ ID NO 29
<211> LENGTH: 26
<212> TYPE: DNA
<213> ORGANISM: Homo sapiens

<400> SEQUENCE: 29
gcggcctgca gggtgacgtt cgttgg                                             26

<210> SEQ ID NO 30
<211> LENGTH: 36
<212> TYPE: DNA
<213> ORGANISM: Homo sapiens

<400> SEQUENCE: 30
ccggcggatc ccatatgtct tacaaccacc tgcagg                                  36

<210> SEQ ID NO 31
<211> LENGTH: 34
<212> TYPE: DNA
<213> ORGANISM: Homo sapiens

<400> SEQUENCE: 31
cgcgcgatat cttattaaga gtgtaccacc attg                                    34

<210> SEQ ID NO 32
<211> LENGTH: 426
<212> TYPE: DNA
<213> ORGANISM: Homo sapiens

<400> SEQUENCE: 32
atgtcttaca accacctgca gggtgacgtt cgttggcgta aactgttctc cttcaccaaa        60
tacttcctga aaatcgaaaa aaacggtaaa gtttctggta ccaagaaaga aaactgcccg       120
tactccatcc tggaaatcac ctccgttgaa atcggtgttg ttgctgttaa agctatcaac       180
tccaactact acctggctat gaacaagaaa ggtaaactgt acggttccaa agaatttaac       240
aacgactgta aactgaaaga acgtatcgaa gaaaacggtt acaacaccta cgcttccttc       300
aactggcagc acaacggtcg acaaatgtat gtggcactga acgtaaaggg tgctccacgt       360
cgtggtcaga aaacccgtcg taaaaacacc tctgctcact ttctgccaat ggtggtacac       420
tcttaa                                                                  426

<210> SEQ ID NO 33
<211> LENGTH: 141
<212> TYPE: PRT
<213> ORGANISM: Homo sapiens

<400> SEQUENCE: 33

Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr

-continued

```
                50                     55                     60
Leu Ala Met Asn Lys Lys Gly Lys Leu Tyr Gly Ser Lys Glu Phe Asn
 65                      70                     75                     80

Asn Asp Cys Lys Leu Lys Glu Arg Ile Glu Glu Asn Gly Tyr Asn Thr
                 85                     90                     95

Tyr Ala Ser Phe Asn Trp Gln His Asn Gly Arg Gln Met Tyr Val Ala
                100                    105                    110

Leu Asn Gly Lys Gly Ala Pro Arg Arg Gly Gln Lys Thr Arg Arg Lys
            115                    120                    125

Asn Thr Ser Ala His Phe Leu Pro Met Val Val His Ser
130                     135                    140
```